United States Patent
Kopylov

(10) Patent No.: US 10,559,378 B2
(45) Date of Patent: Feb. 11, 2020

(54) SYSTEMS AND METHODS FOR PROCESSING LARGE MEDICAL IMAGE DATA

(71) Applicant: AGFA HEALTHCARE NV, Mortsel OT (BE)

(72) Inventor: Viktor Kopylov, Waterloo (CA)

(73) Assignee: AGFA HEALTHCARE NV, Mortsel (BE)

( * ) Notice: Subject to any disclaimer, the term of this patent is extended or adjusted under 35 U.S.C. 154(b) by 180 days.

(21) Appl. No.: 15/436,079

(22) Filed: Feb. 17, 2017

(65) Prior Publication Data

US 2018/0239867 A1 Aug. 23, 2018

(51) Int. Cl.
| | |
|---|---|
| G06F 19/00 | (2018.01) |
| G06T 3/40 | (2006.01) |
| G06T 7/00 | (2017.01) |
| G06K 9/46 | (2006.01) |
| G16H 30/20 | (2018.01) |

(52) U.S. Cl.
CPC ........... *G16H 30/20* (2018.01); *G06K 9/4604* (2013.01); *G06T 3/4092* (2013.01); *G06T 7/0012* (2013.01)

(58) Field of Classification Search
None
See application file for complete search history.

(56) References Cited

U.S. PATENT DOCUMENTS

| | | | |
|---|---|---|---|
| 6,272,235 B1 | 8/2001 | Bacus et al. | |
| 6,574,629 B1 | 6/2003 | Cooke, Jr. et al. | |
| 6,675,271 B1 | 1/2004 | Xu et al. | |
| 6,678,703 B2 | 1/2004 | Rothschild et al. | |
| 6,711,283 B1 | 3/2004 | Soenksen | |
| 6,938,211 B1 | 8/2005 | Chang et al. | |
| 7,386,462 B2 | 6/2008 | Silva-Craig et al. | |
| 7,583,861 B2 | 9/2009 | Hanna et al. | |
| 7,899,884 B2 | 3/2011 | Eichenseer | |
| 7,970,203 B2 | 6/2011 | Avinash et al. | |
| 8,086,077 B2 | 12/2011 | Eichhorn | |
| 8,649,578 B2 | 2/2014 | Yang | |

(Continued)

FOREIGN PATENT DOCUMENTS

| | | |
|---|---|---|
| AU | 2013101075 A4 | 9/2013 |
| EP | 2735982 A1 | 5/2014 |
| WO | 2005050519 A1 | 6/2005 |

OTHER PUBLICATIONS

Non-final Office Action and Notice of References Cited dated Feb. 21, 2019 in related U.S. Appl. No. 15/436,180, (43 pages).

(Continued)

*Primary Examiner* — YuJang Tswei
(74) *Attorney, Agent, or Firm* — Lewis Rice LLC

(57) ABSTRACT

A system and method for managing medical image data items. Pixel data and metadata are identified in the medical image data items. A plurality of pixel objects are generated using the pixel data. The plurality of pixel objects are stored in a first storage memory. A plurality of representative objects are generated using the metadata. The representative objects are stored in a second storage memory. The representative objects may include overview objects and representative metadata objects. The representative objects can be generated in a DICOM-compatible format suitable for PACS workflows.

25 Claims, 9 Drawing Sheets

(56) References Cited

U.S. PATENT DOCUMENTS

| | | | |
|---|---|---|---|
| 8,682,046 | B2 | 3/2014 | Kajimoto et al. |
| 8,731,260 | B2 | 5/2014 | Crandall et al. |
| 9,020,304 | B2 * | 4/2015 | Dorn .................. G06F 19/321 382/305 |
| 2006/0010013 | A1 | 1/2006 | Yamatake |
| 2006/0083442 | A1 | 4/2006 | Loukipoudis et al. |
| 2006/0167945 | A1 | 7/2006 | Trautner |
| 2007/0286330 | A1 | 12/2007 | Boing et al. |
| 2008/0010322 | A1 | 1/2008 | Lee et al. |
| 2008/0021931 | A1 | 1/2008 | Konig |
| 2008/0068673 | A1 | 3/2008 | Kolbu et al. |
| 2008/0147860 | A1 | 6/2008 | Edwards et al. |
| 2008/0168195 | A1 | 7/2008 | Feihl |
| 2009/0074274 | A1 | 3/2009 | Berreth |
| 2009/0287504 | A1 | 11/2009 | Benjamin et al. |
| 2010/0036879 | A1 | 2/2010 | Friese et al. |
| 2010/0235323 | A1 * | 9/2010 | Zhang ................ G06F 19/321 707/623 |
| 2011/0055148 | A1 | 3/2011 | Berg et al. |
| 2013/0191487 | A1 | 7/2013 | Yiu et al. |
| 2016/0206273 | A1 | 7/2016 | Fukuda |
| 2016/0300015 | A1 | 10/2016 | Natarajan et al. |
| 2017/0038951 | A1 * | 2/2017 | Reicher ............... G06F 16/245 |
| 2017/0227564 | A1 * | 8/2017 | Muschler ............. C12M 41/48 |

OTHER PUBLICATIONS

International Search Report and Written Opinion dated May 18, 2018 in related International Patent Application No. PCT/EP2018/053431, (16 pages).

International Search Report and Written Opinion dated Nov. 6, 2018 in corresponding International Patent Application No. PCT/EP2018/053438, (11 pages).

Hastings et al., "A Grid-Based Image Archival and Analysis System", Journal of the American Medical Informatics Association, 2005, 12(3): 286-295, (10 pages).

Clunie et al., "Technical Challenges of Enterprise Imaging: HIMSS-SIIM Collaborative White Paper", Journal of Digital Imaging, 2016, 29(5): 583-614, (32 pages).

International Search Report and Written Opinion dated May 14, 2018 in related International Patent Application No. PCT/EP2018/053447, (10 pages).

Björn, "Enterprise Imaging and Multi-Departmental PACS", European Radiology, 2006, 16(12): 2775-2791, (17 pages).

Non-final Office Action and Notice of References Cited dated Jun. 26, 2019 in related U.S. Appl. No. 15/436,048 (10 pages).

Final Office Action and Notice of References Cited dated Jun. 13, 2019 in related U.S. Appl. No. 15/436,180 (48 pages).

Final Office Action and Notice of Reference Cited dated Oct. 29, 2019 in related U.S. Appl. No. 15/436,180 (68 pages).

* cited by examiner

SYSTEMS AND METHODS FOR PROCESSING LARGE MEDICAL IMAGE DATA

FIELD

The described embodiments relate generally to managing medical data, and in particular to systems and methods for managing large medical image data items, systems and methods for collecting medical image data items, and systems and methods for processing medical image data items.

BACKGROUND

The following is not an admission that anything discussed below is part of the prior art or part of the common general knowledge of a person skilled in the art.

Electronic file management systems are increasingly used to manage medical records. These systems are used to facilitate and streamline various processes such as generating, storing, archiving, searching, reviewing, and reporting electronic medical records. As the size of electronic medical records increases, effective systems for managing and organizing electronic medical records are needed to avoid inefficiencies and backlogs in data transmission and communication. Inefficient or slow file management systems may have a direct impact on clinical efficiency, for instance by increasing the time required for a clinician to retrieve and review each patient file.

A Picture Archiving and Communication System (PACS) provides storage and management of medical image data items. The PACS defines a universal Digital Imaging and Communication in Medicine ("DICOM") format for communication (e.g. storage and transmission) of image files and related metadata. PACS systems are used in many healthcare disciplines such as, but not limited to, radiology, computed tomography, positron emission tomography, magnetic resonance imaging, ultrasonography, and cardiology. As a result, the DICOM standard and DICOM messaging play a key role in modern digital healthcare, along with other communication protocols such as Health Level Seven International (HL7) standards and Fast Healthcare Interoperability Resources (FHIR) standard.

Medical disciplines involving the collection and review of medical images have increasingly been transitioning to electronic and digital imaging systems. Pathology is one example of such a discipline. Pathology is the study of disease in the human tissue and pathology results are often used as critical test results for diagnostic and therapeutic decisions (e.g. HER2 tissue measures needed to allow for the prescription of certain cancer medications). Pathology can involve microscopic, macroscopic, chemical (molecular biology), and biological analysis of tissue samples.

To cope with increasing workloads, high volume pathology departments are digitizing tissue sample slides as high resolution whole slide images (WSI). These digitized slides are used to reorganize clinical routines and procedures and can also be used in clinical research. The convergence of laboratory medicine, anatomical pathology and digital imaging with biomarker data is dramatically changing how pathology and laboratory medicine is practiced. These in vivo and in vitro diagnostics often need to be translated into integrated reports with data collected from various sources.

In pathology, the transformation to the digital world has been enabled by commercially available digitizing imagers used to digitize microscope slides. Each digitizing imager generates a digital representation of the microscopic slide in one or more data files that together form an electronic medical image data item. However, the transformation to electronic medical images and medical image data items is not without technical challenges.

Different medical imagers may generate medical image data items in different and sometimes proprietary formats. While some of these imaging formats are based on open-source imaging specifications (e.g. TIFF, JPEG, BMP, etc.) with proprietary modifications, others use data formats that are entirely proprietary. As a result, different viewing applications may be required to view medical image data items generated by the different viewers.

Generating medical image data items in different formats may also complicate or limit the ability to integrate medical image data items from different imagers into centralized file management systems for managing medical images, such as a PACS. This may result in electronic workflows being limited to particular departments or laboratories that generate medical image data items in the format defined by a particular file management system. As a result, the electronic workflows may only cover a portion of the necessary steps required for a particular imaging task.

For example, in the case of ultrasound guided biopsies, a tissue acquisition workflow forms part of the PACS system, while the sample processing workflow is outside of the PACS and is thus not visible to the PACS. The same may be true for CT/MR or Endoscopy guided sampling procedures. As a result multiple independent electronic workflows (that may not communicate with another) may be required for a single imaging procedure.

It may be difficult for a clinician to obtain a holistic view of related medical image data items available for the same patient or same type of image when the different imagers and imaging workflows are not integrated into a centralized system. For example, in the case of breast tissue sampling a sample from the same tissue block may be used both to create a microscope slide and to undergo X-Ray imaging. However, the X-Ray image may not be available in the pathology image management system while the pathology is not available in the X-Ray image management system.

A clinician using one image management system may be unable to access images from other systems directly, which may introduce delays as they have to change programs or devices to access the other systems. In some cases, the clinician may not be aware that other images have been captured or are available on other file systems, which could lead to oversights or errors.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

According to one broad aspect, there is provided system for managing medical image data items. The system comprises a picture archiving and communication system (PACS) that includes an image storage memory that is configured to store medical image data items, and the PACS is communicatively coupled to at least one viewing station; a large image manager component in communication with the PACS and with at least one medical imager, the large image manager component including a large image storage memory; wherein the large image manager component is configured to: identify large medical image data items generated by the at least one medical imager; and store pixel data from each of the large medical image data items in the large image storage memory; generate at least one representative data object for each of the large medical image data items; and transmit the at least one representative data object for each of the large medical image data items to the PACS; and the PACS is configured to: store the at least one representative data object for each of the large medical image data items in the image storage memory.

In some embodiments, the PACS is configured to: receive a request for a particular medical image from one of the viewing stations; determine that the particular medical image corresponds to one of the large medical image data items stored in the large image storage memory; and re-route the request for the particular medical image to the large image manager component; and the large image manager component is configured to provide particular pixel data corresponding to the particular medical image from the pixel data stored for the corresponding large medical image data item to the viewing station in response to the re-routed request.

In some embodiments, the large image manager component is further configured to: determine that a new large medical image data item has been generated at one of the medical imagers, the new large medical image data item including pixel data defining one or more sub-images and metadata corresponding to the one or more sub-images; extract the metadata from the new large medical image data item; generate the at least one representative data object corresponding to the new large medical image data item to include at least a portion of the extracted metadata; and transmit the at least one representative data object to the PACS; and the PACS is configured to store the at least one representative data object in the image storage memory.

In some embodiments, the large image manager component is configured to: determine that a new large medical image data item has been generated at one of the medical imagers, the new large medical image data item including pixel data defining one or more sub-images and metadata corresponding to the one or more sub-images; extract the pixel data from the new large medical image data item; and store the extracted pixel data in the large image storage memory.

In some embodiments, the large image manager component is further configured to: store the new large medical image data item in an image archive of the large image storage memory; and the extracted pixel data is stored in a processed data cache in the large image storage memory.

In some embodiments, the large image manager component is configured to generate the at least one representative data object to include address metadata identifying a location of the pixel data corresponding to the new large medical image data item; and the PACS is configured to: identify the at least one representative data object in response to receiving a request for a particular medical image corresponding to the new large medical image data item from one of the viewing stations; identify the location of the stored pixel data from the address metadata in the at least one representative data object; and re-route the request for the particular medical image to the large image manager component using the identified location.

In some embodiments, re-routing the request for the particular medical image data item comprises providing the viewing station with a routing response indicating the identified location of the stored pixel data corresponding to the particular medical image.

In some embodiments, re-routing the request for the particular medical image data item comprises automatically re-routing, by the PACS, the request to the large image manager component in response to receiving a request for pixel data from the viewing station.

In some embodiments, the PACS is configured to: define a plurality of large medical imager types, the plurality of large medical imager types including medical imagers configured to generate large medical image data items; determine from the received request that the particular medical image data item was generated by a medical imager corresponding to one of the large medical imager types; and automatically re-route the request to the large image manager component in response to determining that the particular medical image data item was generated by a medical imager corresponding to one of the large medical imager types.

In some embodiments, the large medical image data item includes a plurality of sub-images of medical image series; and the large image manager component is configured to: store image-specific pixel data for each of the sub-images in the plurality of sub-images in the medical image series, wherein the image-specific pixel data for at least some of the sub-images are stored separately from the image-specific pixel data for others of the sub-images.

In some embodiments, the received request identifies one of the sub-images of the medical image series corresponding to the particular medical image; and the large image manager component is configured to provide the image-specific pixel data for the requested sub-image in response to the re-routed request.

In some embodiments, the large image manager component is configured to provide the pixel data corresponding to the particular medical image directly to the viewing station in response to the re-routed request.

In some embodiments, the large image manager component is configured to provide the pixel data corresponding to the particular medical image to the viewing station via the PACS in response to the re-routed request.

In some embodiments, the PACS is configured to communicate using a PACS communication protocol; the medical imager is configured to generate large medical image data items in a format that is different from the format defined by the PACS communication protocol; and the large image manager component is configured to generate the at least one representative data object in the format defined by the PACS communication protocol.

In accordance with a broad aspect, there is provided a method of managing medical image data items using a picture archiving and communication system (PACS) that includes an image storage memory configured to store medical image data items and a large image manager component in communication with the PACS that includes a large image storage memory. The method comprises identifying large medical image data items generated by at least one medical imager; storing pixel data corresponding to each of the large medical image data items in the large image storage memory; generating, by the large image manager component, at least one representative data object for each of the large medical image data items; transmitting, by the large image manager component, the at least one representative data object for each of the large medical image data items to the PACS; and storing the at least one representative data object for each of the large medical image data items in the PACS.

In some embodiments, the method further comprises: receiving, by the PACS, a request for a particular medical image from a viewing station; determining that the particular medical image corresponds to one of the large medical image data items stored in the large image storage memory; re-routing the request for the particular medical image to the large image manager component; and providing, by the large image manager component, particular pixel data corresponding to the particular medical image from the pixel data stored for the corresponding large medical image data item to the viewing station in response to the re-routed request.

In some embodiments, the method further comprises: determining that a new large medical image data item has been generated at one of the medical imagers, the new large medical image data item including pixel data defining one or more sub-images and metadata corresponding to the one or more sub-images; extracting the metadata from the new large medical image data item; generating the at least one representative data object corresponding to the new large medical image data item to include at least a portion of the extracted metadata; and storing the at least one representative data object in the PACS.

In some embodiments, the method further comprises: determining that a new large medical image data item has been generated at one of the medical imagers, the new large medical image data item including pixel data defining one or more sub-images and metadata corresponding to the one or more sub-images; extracting the pixel data from the new large medical image data item; and storing the extracted pixel data in the large image storage memory.

In some embodiments, the method further comprises: storing the new large medical image data item in an image archive of the large image storage memory; and wherein the extracted pixel data is stored in a processed data cache in the large image storage memory. In some such embodiments, the extracted metadata can also be stored in the processed data cache.

In some embodiments, the method further comprises: generating the at least one representative data object to include address metadata identifying a location of the pixel data corresponding to the new large medical image data item; identifying, by the PACS, the at least one representative data object in response to receiving a request for a particular medical image corresponding to the new large medical image data item from one of the viewing stations; identifying, by the PACS, the location of the stored pixel data from the address metadata in the at least one representative data object; and re-routing, by the PACS, the request for the particular medical image to the large image manager component using the identified location.

In some embodiments, re-routing the request for the particular medical image data item comprises providing the viewing station with a routing response indicating the identified location of the stored pixel data corresponding to the particular medical image.

In some embodiments, re-routing the request for the particular medical image data item comprises automatically re-routing, by the PACS, the request to the large image manager component in response to receiving a request for pixel data from the viewing station.

In some embodiments, the method further comprises: defining a plurality of large medical imager types, the plurality of large medical imager types including medical imagers configured to generate large medical image data items; determining, by the PACS, from the received request that the particular medical image data item was generated by a medical imager corresponding to one of the large medical imager types; and automatically re-routing, by the PACS, the request to the large image manager component in response to determining that the particular medical image data item was generated by a medical imager corresponding to one of the large medical imager types.

In some embodiments, the large medical image data item includes a plurality of sub-images of a medical image series and the method further comprises: storing image-specific pixel data for each of the sub-images in the plurality of sub-images in the medical image series, wherein the image-specific pixel data for at least some of the sub-images are stored separately from the image-specific pixel data for others of the sub-images.

In some embodiments, the received request identifies one of the sub-images of the medical image series corresponding to the particular medical image; and providing, by the large image manager component, the particular pixel data corresponding to the particular medical image comprises providing the image-specific pixel data for the requested sub-image in response to the re-routed request.

In some embodiments, providing, by the large image manager component, the particular pixel data corresponding to the particular medical image comprises providing the particular pixel data directly to the viewing station in response to the re-routed request.

In some embodiments, providing, by the large image manager component, the particular pixel data corresponding to the particular medical image comprises providing the particular pixel data to the viewing station via the PACS in response to the re-routed request.

In some embodiments, the PACS is configured to communicate using a PACS communication protocol; the medical imager is configured to generate large medical image data items in a format that is different from the format defined by the PACS communication protocol; and the large image manager component is configured to generate the at least one representative data object in the format defined by the PACS communication protocol.

In accordance with another broad aspect there is provided a computer program product comprising a non-transitory computer-readable storage medium storing computer-executable instructions for configuring a processor to perform a method of managing medical image data items, wherein the method is defined herein.

In accordance with another broad aspect there is provided a method of collecting medical image data items. The method comprises identifying, by a central processor, a new medical image data file on a remote image storage memory that is remote from the central processor; defining, by the central processor, a unique file identifier for the new medical image data file; determining, by the central processor, that the new medical image data file is a complete data file by determining that storage of the new medical image data file on the remote image storage memory has completed; copying the completed data file to a central storage memory in communication with an image management system; storing the unique file identifier of the copied data file in an image source database on the central storage memory; identifying an expected set of medical image data files corresponding to the copied data file, the expected set of medical image data files defining a medical image data item and including at least one medical image data files including the copied data file; defining a unique set identifier for the set of medical image data files defining the medical image data item, the unique set identifier identifying the unique file identifiers for each of the medical image data files in that medical image data item; determining that each of the medical image data files for the medical image data item have been copied to the central storage memory; and generating an indicator that the medical image data item is available for the image management system at the central storage memory.

In some embodiments, identifying the new medical image data file comprises: identifying, by the central processor, a set of image data files stored on the remote image storage memory; determining, by the central processor, remote file identifiers corresponding to the image data files in the set of image data files stored on the remote image storage memory; comparing, by the central processor, the remote file identifiers to the unique file identifiers stored in the image source database; identifying the new medical image data file, by the central processor, as one of the image data files having a remote file identifier that does not match any of the unique file identifiers stored in the image source database.

In some embodiments, the method further comprises: monitoring, by the central processor, the set of image data files stored on the remote image storage memory; determining, from the monitoring, that additional files are stored on the remote image storage memory; and determining, by the central processor, the remote file identifiers as the file identifiers of the additional files such that the new medical image data file is identified from amongst the additional files.

In some embodiments, determining that storage of the new medical image data file on the remote image storage memory has completed comprises: determining file characteristics of the new medical image data file on the remote image storage memory; determining a file type of the new medical image data file, the file type indicating a type of medical image data item defined by the set of medical image data files; determining a complete set of file characteristics for the determined file type; comparing the file characteristics to the complete set of file characteristics; and determining that storage of the new medical image data file on the remote image storage memory has completed when the file characteristics match the complete set of file characteristics.

In some embodiments, determining that storage of the new medical image data file on the remote image storage memory has completed comprises: determining file characteristics of the new medical image data file on the remote image storage memory; subsequently determining updated file characteristics of the new medical image data file on the remote image storage memory; comparing the file characteristics to the updated file characteristics; and determining that storage of the new medical image data file on the remote image storage memory has completed when the file characteristics match the updated file characteristics.

In some embodiments, the method further comprises: allocating the new medical image data file to a new file set upon identifying the new medical image data file, the new file set including an ordered plurality of medical image data files; determining the file characteristics of the new medical image data file on the remote image storage memory at the time of allocating the new medical image data file to the new file set; determining that the new medical image data file has reached a to be copied position in the new file set indicating that the new medical image data file is to be copied to the central storage memory; and determining the updated file characteristics of the new medical image data file upon the new medical image data file reaching the to be copied position.

In some embodiments, the medical image data file is associated with a medical imager type; and the expected set of medical image data files is determined from the medical imager type.

In some embodiments, the unique file identifier for the new medical image data file is defined by the central processor independent of file characteristics of the new medical image data file defined in the remote image storage memory.

In some embodiments, the central processor is prevented from modifying files on the remote image storage memory.

In some embodiments, subsequent to each of the medical image data files for the medical image data item being copied to the central storage memory, the central processor is configured to ignore deletion from the remote image storage memory of any of the medical image data files for the medical image data item.

In some embodiments, the central processor is configured to store each of the medical image data files for the medical image data item in their original format on the central storage memory. In some embodiments, the central processor is prevented from modifying the medical image data files stored on the central storage memory in their original format. In some embodiments, the central processor generates a digital signature for each of the medical image data files stored in their original format, wherein the digital signature for a particular medical image data file indicates that the particular medical image data file has not been modified.

In some embodiments, the method further comprises: determining, by the central processor, for an additional medical image data item that at least one additional medical image data file in an expected set of additional medical image data files defining the additional medical image data item will not be available for copying from the remote storage memory; and deleting any of the additional medical image data items already copied to the central storage memory.

In accordance with a broad aspect there is provided an image collection system comprising: a central storage memory having an image storage section and an image source database, the central storage memory in communication with an image management system; and a central processor coupled to the central storage memory and to a remote image storage memory that is remote from the central processor and from the central storage memory, wherein the central processor is configured to: identify a new medical image data file on the remote image storage memory; define a unique file identifier for the new medical image data file; determine that the new medical image data file is a complete data file by determining that storage of the new medical image data file on the remote image storage memory has completed; copy the completed data file to the image storage section; store the unique file identifier of the copied data file in the image source database; identify an expected set of medical image data files corresponding to the copied data file, the expected set of medical image data files defining a medical image data item and including at least one medical image data files including the copied data file; define a unique set identifier for the set of medical image data files defining the medical image data item, the unique set identifier identifying the unique file identifiers for each of the medical image data files in that medical image data item; determine that each of the medical image data files for the medical image data item have been copied to the image storage section; and generate an indicator that the medical image data item is available for the image management system on the central storage memory.

In some embodiments, the central processor is configured to identify the new medical image data file by: identifying a set of image data files stored on the remote image storage memory; determining remote file identifiers corresponding to the image data files in the set of image data files stored on the remote image storage memory; comparing the remote file identifiers to the unique file identifiers stored in the image source database; and identifying the new medical image data file as one of the image data files having a remote file identifier that does not match any of the unique file identifiers stored in the image source database.

In some embodiments, the central processor is configured to: monitor the set of image data files stored on the remote image storage memory; determine, from the monitoring, that additional files are stored on the remote image storage memory; determine the remote file identifiers as the file identifiers of the additional files such that the new medical image data file is identified from amongst the additional files.

In some embodiments, the central processor is configured to determine that storage of the new medical image data file on the remote image storage memory has completed by: determining file characteristics of the new medical image data file on the remote image storage memory; determining a file type of the new medical image data file, the file type indicating a type of medical image data item defined by the set of medical image data files; determining a complete set of file characteristics for the determined file type; comparing the file characteristics to the complete set of file characteristics; and determining that storage of the new medical image data file on the remote image storage memory has completed when the file characteristics match the complete set of file characteristics.

In some embodiments, the central processor is configured to determine that storage of the new medical image data file on the remote image storage memory has completed by: determining file characteristics of the new medical image data file on the remote image storage memory; subsequently determining updated file characteristics of the new medical image data file on the remote image storage memory; comparing the file characteristics to the updated file characteristics; and determining that storage of the new medical image data file on the remote image storage memory has completed only if the file characteristics match the updated file characteristics.

In some embodiments, the central processor is further configured to: allocate the new medical image data file to a new file set upon identifying the new medical image data file, the new file set including an ordered plurality of medical image data files; determine the file characteristics of the new medical image data file on the remote image storage memory at the time of allocating the new medical image data file to the new file set; determining that the new medical image data file has reached a to be copied position in the new file set indicating that the new medical image data file is to be copied to the image storage section; and determining the updated file characteristics of the new medical image data file upon the new medical image data file reaching the to be copied position.

In some embodiments, the medical image data file is associated with a medical imager type; and the central processor is configured to determine the expected set of medical image data files from the medical imager type associated with the medical image data file.

In some embodiments, the central processor is configured to define the unique file identifier for the new medical image data file independent of file characteristics of the new medical image data file defined in the remote image storage memory.

In some embodiments, the central processor is prevented from modifying files on the remote image storage memory.

In some embodiments, the central processor is configured to ignore deletion of any of the medical image data files for the medical image data item from the remote image storage memory once each of the medical image data files for the medical image data item has been copied to the image storage section.

In some embodiments, the central processor is configured to store each of the medical image data files for the medical image data item in their original format on the central storage memory. In some embodiments, the central processor is prevented from modifying the medical image data files stored on the central storage memory in their original format. In some embodiments, the central processor generates a digital signature for each of the medical image data files stored in their original format, wherein the digital signature for a particular medical image data file indicates that the particular medical image data file has not been modified.

In some embodiments, the central processor is further configured to: determine for an additional medical image data item that at least one additional medical image data file in an expected set of additional medical image data files defining the additional medical image data item will not be available for copying from the remote storage memory; and delete any of the additional medical image data items already copied to the central storage memory.

In accordance with a broad aspect there is provided a computer program product comprising a non-transitory computer-readable storage medium storing computer-executable instructions for configuring a processor to perform a method of collecting medical image data items, wherein the method is defined herein.

In accordance with a broad aspect there is provided a method of managing medical image data items. The method comprises: receiving a medical image data item, the medical image data item including at least one medical image set where each medical image set in the at least one medical image set is from the same medical imaging procedure and defines a sub-image from the medical imaging procedure, and each medical image set has a corresponding resolution and includes at least one sub-image object; defining a data item identifier for the received medical image data item; analyzing the received medical image data item to identify image metadata and image pixel data; generating a plurality of pixel objects for the medical image data item using the image pixel data, wherein each pixel object includes at least a portion of the image pixel data that corresponds to one of the sub-images, each sub-image has at least one corresponding pixel object, each portion of the image pixel data is included in one of the pixel objects, and each pixel object also includes a pixel object identifier that identifies the data item identifier and the sub-image corresponding to that pixel object; storing the plurality of pixel objects in a first storage memory with each pixel object having an address location in the first storage memory; generating at least one representative object for the medical image data item using the image metadata, the at least one representative object including a set representative object corresponding to each medical image set, and each set representative object defines identifying characteristics for the corresponding sub-image of the medical image set and identifies the first storage memory in which the corresponding at least one pixel object is stored; and storing the at least one representative object in a second storage memory.

In some embodiments, each pixel object corresponds to one of the sub-images and includes all the image pixel data from that sub-image.

In some embodiments, the address location for each pixel object is individually addressable in the first storage memory.

In some embodiments, for each pixel object in the plurality of pixel objects, the address location in the first storage memory at which that pixel object is stored is determined independently from the address location for any of the other pixel objects.

In some embodiments, each set representative object comprises a representative metadata object that includes metadata defining the identifying characteristics for the corresponding sub-image and identifying the first storage memory in which the corresponding at least one pixel object is stored.

In some embodiments, the method further comprises: generating the at least one representative object to include at least one overview object for the medical image data item, wherein each overview object includes an overview pixel object and overview object metadata, the overview pixel object generated from a selected portion of the image pixel data and representing an overview of the medical image sets from the medical imaging procedure with an overview resolution that is less than the resolution of the image pixel data in the at least one medical image sets, and the overview object metadata includes a portion of the image metadata corresponding to the selected portion of the image pixel data and representative object identifiers identifying each of the at least one set representative objects; and storing the at least one overview object in the second storage memory.

In some embodiments, generating the at least one overview object comprises: generating a plurality of overview objects for one of the medical image sets in the medical image data item, wherein each overview object in the plurality of overview objects has an overview pixel object with a different overview resolution.

In some embodiments, the method further comprises: defining overview object accessibility criteria that controls access to each of the overview objects based on the overview object metadata and a role assigned to a user attempting to access the overview objects.

In some embodiments: the second storage memory is accessible using a Picture Archive and Communication System (PACS) that communicates using a defined communication protocol; and each representative object is generated according to the defined communication protocol.

In some embodiments, the received medical image data item is in a format that is not compatible with the defined communication protocol.

In some embodiments, the method further comprises: generating at least one set of pixel metadata objects, each set of pixel metadata objects corresponding to one of the medical image sets, and each set of pixel metadata objects including identifying metadata defining identifying characteristics for the pixel objects corresponding to that medical image set and relational metadata defining spatial relationships between the pixel objects corresponding to that medical image set.

In some embodiments, the method further comprises storing the at least one set of pixel metadata objects in the first storage memory.

In some embodiments, the first storage memory and the second storage memory are remote from one another and are accessible via different image management systems.

In accordance with a broad aspect there is provided a computer program product comprising a non-transitory computer-readable storage medium storing computer-executable instructions for configuring a processor to perform a method of managing medical image data items, wherein the method is defined herein.

In accordance with a broad aspect, there is provided a system for managing medical image data items comprising: a first storage memory; a second storage memory; and at least one processor coupled to the first storage memory and the second storage memory, wherein the at least one processor is configured to: receive a medical image data item, the medical image data item including at least one medical image set where each medical image set in the at least one medical image set is from the same medical imaging procedure and defines a sub-image from the medical imaging procedure, and each medical image set has a corresponding resolution and includes at least one sub-image object; define a data item identifier for the received medical image data item; analyze the received medical image data item to identify image metadata and image pixel data; generate a plurality of pixel objects for the medical image data item using the image pixel data, wherein each pixel object includes at least a portion of the image pixel data that corresponds to one of the sub-images, each sub-image has at least one corresponding pixel object, each portion of the image pixel data is included in one of the pixel objects, and each pixel object also includes a pixel object identifier that identifies the data item identifier and the sub-image corresponding to that pixel object; store the plurality of pixel objects in the first storage memory with each pixel object having an address location in the first storage memory; generate at least one representative object for the medical image data item using the image metadata, the at least one representative object including a set representative object corresponding to each medical image set, and each set representative object defines identifying characteristics for the corresponding sub-image of the medical image set and identifies the first storage memory in which the corresponding at least one pixel object is stored; and store the at least one representative object in the second storage memory.

In some embodiments, the at least one processor is configured to generate each pixel object to correspond to one of the sub-images and to include all the image pixel data from that sub-image.

In some embodiments, the at least one processor is configured to store each pixel object at an individually addressable address location in the first storage memory.

In some embodiments, for each pixel object in the plurality of pixel objects, the at least one processor is configured to determine the address location in the first storage memory at which that pixel object is stored independently from the address location for any of the other pixel objects.

In some embodiments, the at least one processor is configured to generate each set representative object as a representative metadata object that includes metadata defining the identifying characteristics for the corresponding sub-image and identifying the first storage memory in which the corresponding at least one pixel object is stored.

In some embodiments, the at least one processor is configured to: generate the at least one representative object to include at least one overview object for the medical image data item, wherein each overview object includes an overview pixel object and overview object metadata, the overview pixel object generated from a selected portion of the image pixel data and representing an overview of the medical image sets from the medical imaging procedure with an overview resolution that is less than the resolution of the image pixel data in the at least one medical image sets, and the overview object metadata includes a portion of the image metadata corresponding to the selected portion of the image pixel data and representative object identifiers identifying each of the at least one set representative objects; and store the at least one overview object in the second storage memory.

In some embodiments, the at least one processor is configured to generate the at least one overview object by: generating a plurality of overview objects for one of the medical image sets in the medical image data item, wherein each overview object in the plurality of overview objects has an overview pixel object with a different overview resolution.

In some embodiments, the at least one processor is configured to: define overview object accessibility criteria that controls access to each of the overview objects based on the overview object metadata and a role assigned to a user attempting to access the overview objects.

In some embodiments, the second storage memory is accessible using a Picture Archive and Communication System (PACS) that communicates using a defined communication protocol; and the at least one processor is configured to generate each representative object according to the defined communication protocol.

In some embodiments, the received medical image data item is in a format that is not compatible with the defined communication protocol.

In some embodiments, the at least one processor is configured to: generate at least one set of pixel metadata objects, each set of pixel metadata objects corresponding to one of the medical image sets, and each set of pixel metadata objects including identifying metadata defining identifying characteristics for the pixel objects corresponding to that medical image set and relational metadata defining spatial relationships between the pixel objects corresponding to that medical image set.

In some embodiments, the at least one processor is configured to store the at least one set of pixel metadata objects in the first storage memory.

In some embodiments, the first storage memory and the second storage memory are remote from one another and are accessible via different image management systems.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

Figure 1:
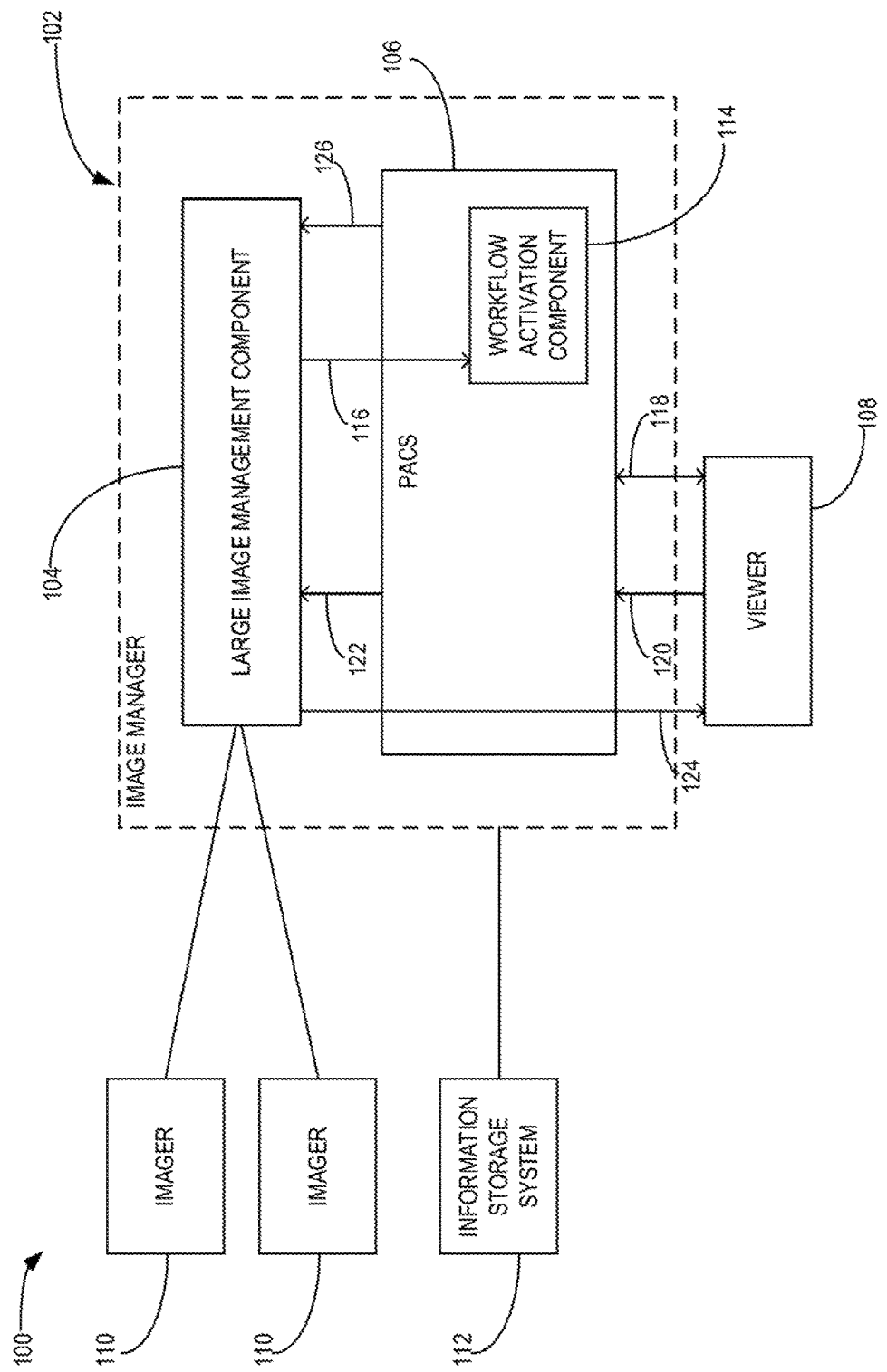
FIG. 1 is a block diagram of an image management system in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXEMPLARY EMBODIMENTS

Various systems, methods and computer program products will be described below to provide an example of an embodiment of the claimed subject matter. No embodiment described below limits any claimed subject matter and any claimed subject matter may cover methods or systems that differ from those described below. The claimed subject matter is not limited to systems or methods having all of the features of any one system or method described below or to features common to multiple or all of the apparatuses or methods described below. It is possible that a system or method described below is not an embodiment that is recited in any claimed subject matter. Any subject matter disclosed in a system or method described below that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling may be used to indicate that an element or device can electrically, optically, or wirelessly send data to another element or device as well as receive data from another element or device.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising," and variations thereof mean "including but not limited to," unless expressly specified otherwise. A listing of items does not imply that any or all of the items are mutually exclusive, unless expressly specified otherwise. The terms "a," "an," and "the" mean "one or more," unless expressly specified otherwise.

Furthermore, any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

The example embodiments of the systems and methods described herein may be implemented as a combination of hardware or software. In some cases, the example embodiments described herein may be implemented, at least in part, by using one or more computer programs, executing on one or more programmable devices comprising at least one processing element, and a data storage element (including volatile memory, non-volatile memory, storage elements, or any combination thereof). These devices may also have at least one input device (e.g. a pushbutton keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level computer programming language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage.

While the use of electronic file management systems is becoming increasingly prevalent in medical disciplines, current image management systems may be ill-equipped to handle the size and volume of medical images being generated. Often, image management systems operate in isolation within a particular department, and medical images generated by different imaging processes or different imagers in other departments may not be apparent or available. For example, different image management systems may operate using different file formats or communication protocols.

In some cases, medical image data items may be converted to a standard format or protocol such as the DICOM standard. While this may permit integration with a centralized image management system such as a PACS, managing large medical image data items may still present technical challenges. The existing core PACS architecture (and legacy systems) can be ill-equipped for the increases in performance, throughput, and volume that are often required to manage large medical image data items, especially at high volume.

Core PACS workflows and storage policies may not be configured to support the network bandwidth and storage capabilities associated with large medical image data items. Because the DICOM standard is primarily concerned with the standardization of data transmission/communication, the protocol is not defined with a focus on the issues of storage, retrieval, and display performance and feasibility that are at the forefront of managing large medical image data items.

While updating the core PACS architecture could alleviate some of these problems, this is a lengthy and expensive process. Updating the core PACS architecture often requires extensive development, verification, validation, and regulatory approval. All the while, additional medical image data items are generated, and the medical image data items continue to grow in size.

For example, consider a tissue slide sample of about 20 mm×15 mm in size. This sample may be digitized with a resolution of 0.25 micrometers/pixel (microns per pixel or mpp) which may generally correspond to an optical microscope having 400× magnification. The resulting medical image may be about 80,000 pixels×60,000 pixels or 4.8 GigaPixels. The corresponding digital medical image generated in 24-bit color may then have a data size of about 15 GB.

Even larger data size medical image data items may also be generated by medical imagers. For example, tissue sample sizes up to 50 mm×25 mm may be captured from conventional 1"×3" tissue slides, and even larger sample sizes may exist on 2"×3" tissue slides. Medical images may also be digitized at resolutions higher than 0.25 mpp—for instance, some scanning instruments now support oil immersion lenses which can magnify up to 100×, yielding about 0.1 mpp resolution.

For some sample types, a tissue sample may be thicker than the depth of field of the objective lens. As a result, multiple focal planes ("Z planes") may be captured as sub-images of the medical image generated for the tissue sample. A tissue sample of 50 mm×25 mm may be digitized into a medical image data item at 0.1 mpp with 10 Z-planes, resulting in a medical image data item that includes 10 sub-images of dimension 500,000×250,000 pixels each. Each plane sub-image would be about 125 Gp, or 375 GB of data, and the entire medical image data item would be about 3.75 TB of data. Additionally, multispectral imaging may capture up to 10 spectral bands at 16-bit per pixel resolution.

As resolution increases, and the ability to capture more sub-image (e.g. additional z-planes) also increases, the data size of medical image data items will continue to increase. Accordingly, medical image management systems may need to adapt to facilitate procedures using these large medical image data items.

Embodiments described herein may provide a centralized system configured to access and manage medical image data items generated by different imagers and in different formats. This system may provide centralized access to medical images that would previously have been accessible only through department specific file management systems. Embodiments described herein may also provide systems and methods that are capable of identifying, collecting, processing and managing a wide array of large medical image data items. The described embodiments may alleviate some of the inefficiencies of current systems for managing medical image data items.

Embodiments of the systems, methods and computer program products described herein generally relate to managing medical image data items. As used herein, the term "medical image data item" refers to the set of electronic data that defines an electronic medical image. A medical image data item is formed by a set of files that includes one or more electronic files which together include all the pixel data and metadata defining the medical image (possible including multiple sub-images) and associated properties.

In general, medical image data items are generated by medical imagers. An individual medical image data item generally corresponds to a medical imaging procedure, such as digitizing a tissue sample slide, performing an X-Ray or Computed-Tomography scan, or capturing an endoscopy video for example. In the example of an endoscopy video, the medical image data item can include sub-images corresponding to each frame of the video.

Medical image data items may also include additional metadata defining characteristics or properties of the medical image, such as patient data or other data retrieved from a hospital information system (HIS), Laboratory/Departmental Information System (LIS), and/or Radiology Information System (RIS). The format of individual medical image data items may differ, and may be modified in various processes described herein.

In particular, embodiments described herein may facilitate collection, processing and/or management of large medical image data items. For example, all medical image data items generated by one or more managers may be stored in a storage component external to the core workflows of an existing image management system. Representative objects can be generated for each of those medical image data items and then provided to the existing image management system to be used in the core workflows. The representative objects can be generated with a data size smaller than the medical image data items themselves to facilitate management within existing workflows. For instance, representative objects may be limited to a maximum data size of 100 MB in some examples. In some examples, the representative objects may be limited to a maximum data size of 10 MB. Embodiments described herein may provide a centralized system that provides clinicians with access to large medical image data items from multiple imagers. In some cases, the centralized system can include medical image data items originally generated by multiple imagers having different imaging types and/or medical image data items originally generated in different formats.

Some embodiments described herein may provide image management systems and methods that operate with existing image management systems. For example, embodiments described herein may operate in conjunction with core components of a PACS system, such as the PACS described in U.S. Pat. No. 6,574,629, the entirety of which is incorporated herein by reference.

Although the description may refer to a PACS system for clarity and brevity, it should be understood that embodiments of the systems and methods described herein may be applied with other medical image management systems unless indicated otherwise. As well, although the description may refer to image management systems operating using a DICOM communication protocol, it should be understood that embodiments of the systems and methods described herein may be applied with image management and file management systems using other defined communication protocols and standards.

Embodiments described herein may provide a large image manager or large image manager component (which may be referred to herein as a "LIM"). The LIM may store large medical image data items in storage memory external to the core components of existing medical image management systems such as a PACS. The large image manager component may provide representative data objects to the medical image management systems (e.g. PACS) representing the large medical image data items stored in the LIM. These representative data objects may then be incorporated into existing image management workflows. The representative data objects can be generated with a limited data size to facilitate incorporating into the workflows. The data size of the representative data objects can be significantly smaller than the data size of large medical image data items stored in the LIM (e.g. 100, 1000, or 10,000 times smaller). When requests for medical images corresponding to the large medical image data items are received by a PACS, the requests can be re-routed to the LIM. The LIM may then process the re-request and provide the pixel data for the requested image.

In embodiments described herein, existing medical image workflows can be used to manage the lifecycle of large medical image data items similar to smaller medical image data items. However, the large medical image data items can be stored, moved and processed externally from the core components that manage the image lifecycle. Thus, the lifecycle of large medical image data items may be managed without introducing delays or bottlenecks due to inefficient transmission of the large medical image data items in the core components of the PACS.

In some embodiments, the LIM may be completely external to the PACS. Alternatively, the LIM may operate as an extension or plug-in within the PACS system. When the LIM operates as an extension or plug-in, it may nonetheless operate outside the workflows of the core PACS system (e.g. by storing large medical image data items in a separate section of memory from the corresponding representative objects used in the workflows).

The LIM may be configured with separate file systems and messaging systems from the PACS. The LIM may also use a different communication protocol from the PACS for its internal file management and image management processes.

The LIM may acquire medical image data items generated by one or more medical imagers. The medical image data items may include data items corresponding to medical images from imagers such as digital pathology scanners, endoscopy video cameras, X-Ray scanners, CT scanners etc. In some cases, the medical image data items may be generated in a DICOM compatible format, such as DICOM WSI. In other cases, the medical image data items may be generated in other formats, such as imager-specific proprietary formats that may not be directly compatible with the DICOM protocol.

In some cases, the LIM may be in communication with the medical imagers directly. Alternatively, the LIM may collect or acquire medical image data items from image storage databases, imaging archives and/or image management systems associated with the medical imagers.

The LIM generally includes one or more processors and a LIM memory. The medical image data items collected by the LIM can be stored in the LIM memory. The LIM may provide access to the medical image data items through an interface that complies with the communication protocol used or defined by the core components of medical image management system such as PACS. For instance, the LIM may include a DICOM interface or API configured to communicate with a PACS in a DICOM compliant manner.

In some embodiments described herein, large medical image data items may be stored separately from smaller medical image data items. For instance, small medical image data items (e.g. those medical image data items below a threshold data size) may be stored in a storage memory that forms part of the core components of a PACS, while large medical image data items (e.g. medical image data items equal to or greater than a threshold data size) are stored in a separated storage memory included in the LIM.

The threshold data size may vary depending on the system configuration and requirements for different individual and organizational users. In some cases, the threshold data size may vary based on network infrastructure configurations and/or data storage considerations for a particular system implementation.

In other embodiments, all of the medical image data items may be stored in the LIM. For example, the original medical image data items may be stored in the LIM in an unmodified or unprocessed state to provide a single repository for the originally captured medical image data items. This may facilitate regulatory compliance for instance, when medical image data items must be stored in their original format.

The LIM may generate representative objects for the collected medical image data items. The representative objects can include DICOM-formatted objects that can be provided to the PACS. The PACS may then use these DICOM representative objects in the core PACS workflows. For instance, the PACS may integrate these DICOM representative objects into its core data lifecycle management and data access workflows. The DICOM representative objects may be integrated into workflows along with the small medical image data items that are stored in the core PACS system.

This may allow the PACS to provide integrated file and lifecycle management for medical image data items from different departments and different imaging procedures. This may also provide a clinician with a centralized database of available medical image data items, as well as centralized access to these medical image data items.

The LIM may integrate with the PACS to modify the workflows for medical image data items stored in the LIM. For instance, when the PACS workflows results in a request to provide, transfer, modify and/or delete a medical image data item, these requests can be re-routed to the LIM to process the request. The LIM may then perform the requested actions or portions of the requested actions involving data stored in the LIM. When the workflows or requests relate to small medical image data items stored in the PACS, the requests can be handled by the core components of the PACS according to conventional workflows in embodiments where those small medical image data items are stored in the PACS. Alternatively, they may still be re-routed to the LIM in embodiments where all of the medical image data items are stored in the LIM.

The LIM may collect medical image data items in an "as-is" state. That is, the LIM may collect medical image data items in the format defined by the imager used to generate those medical image data items. The LIM may also store these collected medical image data items in their original format. These medical image data items may not be modifiable when stored in their "as-is" state. Rather, any processing may be limited to reading and/or extracting the data stored in the original medical image data items.

The LIM memory may include a large image storage archive in which the collected medical image data items can be stored in their original format and original state. This may ensure compliance with regulatory requirements and to provide for data fidelity. The LIM may also generate a digital signature for the collected medical image data items indicating that the stored medical image data items have not been modified from their originally collected state. This may provide assurances that the medical image data items are being stored in accordance with regulatory obligations.

Although the description may describe the operations of the LIM in the context of operating in conjunction with a PACS, it should be understood that various features and components of the LIM may operate independently of a PACS unless indicated otherwise. Similarly, although various systems and methods may be described herein with reference to a PACS and/or LIM, it should be understood that these systems and methods may be implemented in other systems except where indicated otherwise. For instance, systems and methods described herein for collecting medical image data items can be implemented with or without a PACS and/or a LIM. Similarly, systems and methods described herein for processing medical image data items can be implemented with or without a PACS and/or a LIM.

Referring now to FIG. 1, shown therein is a block diagram of an image management system 100 in accordance with an example embodiment. In the example shown in FIG. 1, system 100 includes an imager manager 102 communicatively coupled to imagers 110 and to at least one information storage system 112. The image manager 102 includes a large image management component (LIM) 104 coupled to a picture and archiving communication system (PACS) 106.

In general, system 100 generally includes a plurality of computers that can be connected via a data communication network. The data communication network may include both local and wide communication networks, and may be connected to the internet.

Typically, the connection between the data communication network and the Internet may be made via a firewall server (not shown). In some cases, there may be multiple links or firewalls, or both, between the data communication network and the Internet. Some organizations may operate multiple networks or virtual networks, which can be internetworked or isolated. These have been omitted for ease of illustration, however it will be understood that the teachings herein can be applied to such systems. The networks may be constructed from one or more computer network technologies, such as IEEE 802.3 (Ethernet), IEEE 802.11 and similar technologies.

Computers and computing devices, such as the imagers 110, information storage systems 112, image manager 102 (i.e. LIM 104 and PACS 106), and viewers 108 may be connected to the data communication network or a portion thereof via suitable network interfaces. In some cases, one or more of the computing devices such as the viewers 108 may connect to the data communication network via the Internet.

Examples of computers that may be used to implement components of system 100 such as LIM 104, PACS 106 and viewers 108 can include desktop or laptop computers. These computers can be connected to the data communication network via a wired Ethernet connection or a wireless connection. The imager manager 102 (including large image manager component 104 and PACS 106) may also connect to the data communication network via the Internet.

Viewer 108 has a processor, volatile memory and non-volatile storage memory, at least one network interface, and may include input devices such as a keyboard and trackpad, as well as output devices such as a display and speakers, and various other input/output devices as will be appreciated.

The image manager 102 has at least one processor, volatile memory and non-volatile storage memory, at least one network interface, and may include input devices such as a keyboard and trackpad, as well as output devices such as a display and speakers, and various other input/output devices as will be appreciated. In some cases, the image manager 102 may include multiple linked server computers that are accessible through the data communication network, for example via the Internet. Accordingly, the image manager 102 may not directly require input devices and/or output devices.

The large image manager component 104 also generally includes at least one processor, volatile memory and non-volatile storage memory, and at least one network interface. The large image manager component 104 may be implemented as a combination of hardware and software, and may include software programs may be stored on a storage media or a device that is readable by a general or special purpose programmable device. The LIM 104 may also be distributed amongst multiple instances of processors and/or storage memory.

The PACS 106 also generally includes at least one processor, volatile memory and non-volatile storage memory, and at least one network interface. The PACS 106 may be implemented as a combination of hardware and software, and may include software programs may be stored on a storage media or a device that is readable by a general or special purpose programmable device. The PACS 106 may also be distributed amongst multiple instances of processors and/or storage memory.

In some examples, there may be overlap between the processors and/or memory used by the large image manager component 104 and PACS 106. In other cases, each of the large image manager component 104 and PACS 106 may use completely independent processors and memory. In general, however, the large image manager component 104 operates a separate file system and messaging system from the PACS 106, and has a separate data storage memory. The large image manager component 104 and PACS 106 may communicate using a communication interface, such as DICOM interface 350 shown in FIG. 3 and discussed below.

Some of the computers in system 100, such as the viewer 108, may be implemented by mobile devices such as a smartphone or tablet computer. Mobile devices may generally include a wide variety of "smart" devices capable of data communication. In general, the mobile devices have a processor, volatile and non-volatile memory, at least one network interface, and input/output devices. Mobile devices are typically portable, and may at times be connected to the data communication network or a portion thereof. For instance, the mobile device may connect to the data communication network remotely, using a virtual private network (VPN).

In general, the processors used by the computer components of system 100 can be computer processors, such as a general purpose microprocessor. In some other cases, the processors may include a field programmable gate array, application specific integrated circuit, microcontroller, or other suitable computer processor.

The processors can be coupled, via a computer data bus, to memory. Memory may include both volatile and non-volatile memory. Non-volatile memory stores computer programs consisting of computer-executable instructions, which may be loaded into volatile memory for execution by the processors as needed. It will be understood by those of skill in the art that references herein to components such as LIM 104 or PACS 106 as carrying out a function or acting in a particular way imply that one or more processors is executing instructions (e.g., a software program) stored in memory and possibly transmitting or receiving inputs and outputs via one or more interface. Memory may also store data input to, or output from, the processors in the course of executing the computer-executable instructions.

The processors may also be coupled to one or more displays suitable for outputting information and data as needed by various computer programs. In particular, the displays may display a graphical user interface (GUI) to a user interacting with the image manager 102. For example, the viewer 108 may include a display that provides a GUI for a user to interact with the imager manager 102 via the viewer 108. In some cases, a display may be omitted from LIM 104 or PACS 106, for instance where the LIM 104 or PACS 106 are configured to operate autonomously. In such cases, the LIM 104 or PACS 106 may be configurable using a computer such as the viewer 108 that is connected to the image manager 102. The various components of system 100, such as the LIM 104, PACS 106 and viewer 108 may each execute an operating system, such as Microsoft Windows™ GNU/Linux, or other suitable operating system.

Each of the computers and computing devices used to implement components of system 100 may at times connect to external computers or servers via the Internet. For example, the LIM 104 and/or PACS 106 may connect to external image storage archives that may be stored remotely or "in the cloud".

As used herein, the term "software application" or "application" refers to computer-executable instructions, particularly computer-executable instructions stored in a non-transitory medium, such as a non-volatile memory, and executed by a computer processor. The computer processor, when executing the instructions, may receive inputs and transmit outputs to any of a variety of input or output devices to which it is coupled.

The image manager 102 can be used to provide various functions and operations relating to the storage and management of medical image data items. In particular, the image manager 102 shown in FIG. 1 may facilitate the management of large medical image data items. The image manager 102 may also facilitate the management of medical image data items generated by different imagers and in different imaging file formats.

In some cases, the image manager 102 can be used to implement various processes for managing medical image data items, such as methods 400 and 500 described herein below. In some cases, the image manager 102 can be used to implement various processes for collecting medical image data items, such as method 600 described herein below. In some cases, the image manager 102 can be used to implement various processes for processing medical image data items, such as method 700 described herein below. In some cases, the image manager 102 can be used to implement various processes for transferring medical image data items, such as method 800 described herein below.

The image manager 102 generally includes the large image manager component or LIM 104 and the PACS 106. The LIM 104 and PACS 106 may operate in conjunction to collect, store, retrieve, process, provide access to, and display medical image data items.

Figure 2:
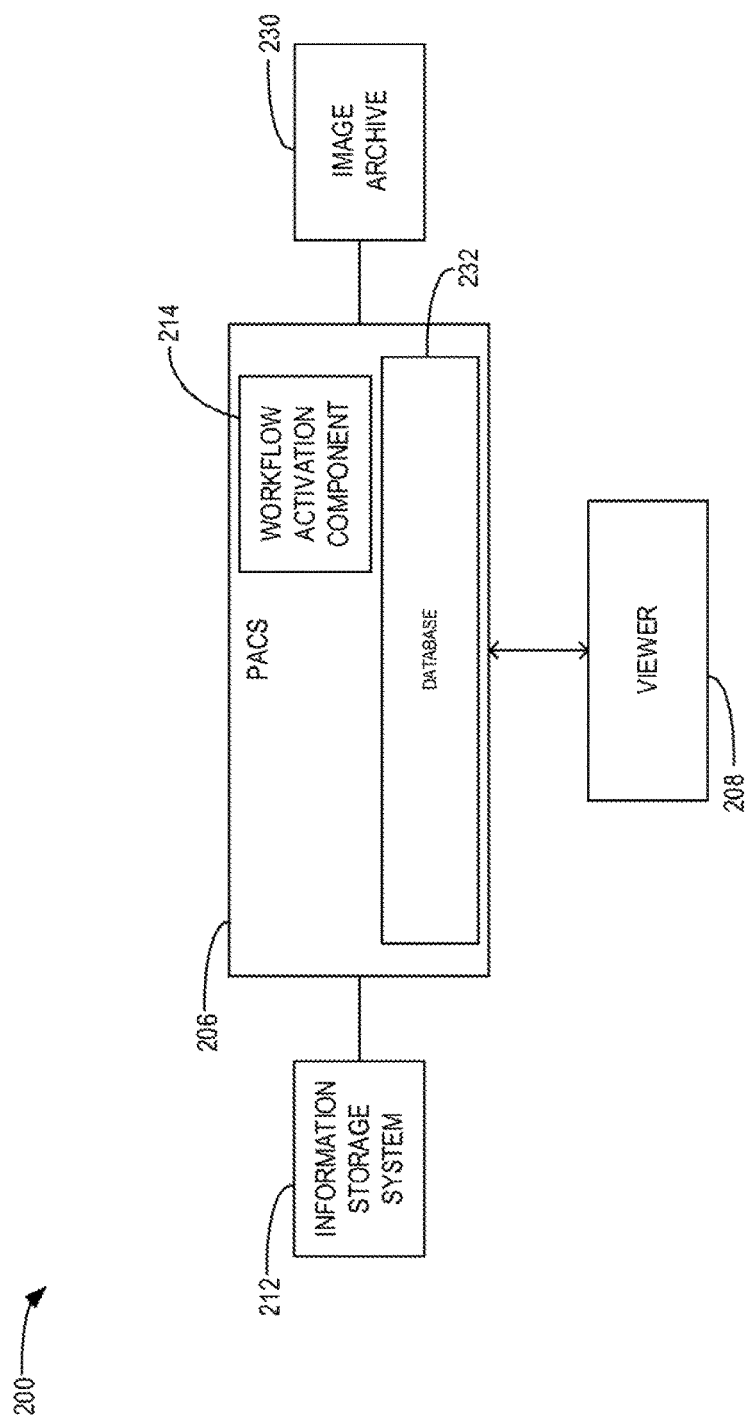
FIG. 2 is a block diagram of an example Picture Archiving and Communication System (PACS)

An example of a PACS 206 that may be used to implement PACS 106 is shown in FIG. 2 and described in further detail below. In general, the PACS 106 includes a number of core components implemented as a combination of hardware and software. These core components provide functions such as archiving, reviewing and displaying medical images. In some cases, the viewer 108 may be considered as a core component of the PACS 106. For example, the core components of PACS 106 may generally correspond to core components of the PACS described in U.S. Pat. No. 6,574,629

The PACS 106 includes a workflow activation component 114 that defines workflows used to manage data stored in the PACS 106. The workflows defined by workflow activation component 114 may be initiated in response to user input, such as a request to review a medical image or to transfer a medical image data item to an external system. The workflows defined by workflow activation component 114 may also be initiated automatically in response to system triggers, such as a period of time elapsing after certain actions have occurred.

The workflows may include lifecycle management workflows, which can define where and how different medical image data items are stored (e.g. how and when medical image data items should be archived, how and when medical image data items should be modified and/or deleted, etc.). The workflows may include image access workflows that can define when and how medical image data items are provided to viewers 108 for review (e.g. how and when medical image data items should be retrieved for access or review, how and when medical image data items should be pre-fetched for expected review, etc.). The workflows may include image transfer workflows that can define when and how medical image data items are transferred between PACS 106 and external image management systems. The workflows can include image collection workflows that can define when and how medical image data items are collected from external image management systems. The workflows can include image processing workflows that can define when and how medical image data items are processed by the imager 102. For example, the image processing workflows in workflow activation component 114 can trigger corresponding image processing workflows in the LIM 104. The workflows can also include image reconciliation workflows that can define when and how medical image data items are updated with external systems, such as laboratory information systems 112

The PACS 106 can include an image storage memory that can be used to store medical image data items, as well as associated information. The image storage memory can store configuration files for the PACS 106 that may be used by the workflow activation component 114 to determine relationships between medical image data items, data collection or transfer rules and destinations, data related to external systems in communication with the PACS 106 as well as other data.

In general, the PACS 106 operates using a defined communication protocol, in this case DICOM. The data stored by the PACS 106 are stored and managed in accordance with the DICOM standard protocol. For instance, workflows defined by the workflow activation component 114 operate in accordance with the DICOM standard.

The PACS 106 may also include external interfaces or gateways to interface with external components such as the LIM 104, viewer 108, imagers 110, and/or information storage system 112. The external interfaces may be configured to receive and transmit data and messages in accordance with defined communication protocols such as DICOM, HL7, FHIR, etc.

Figure 3:
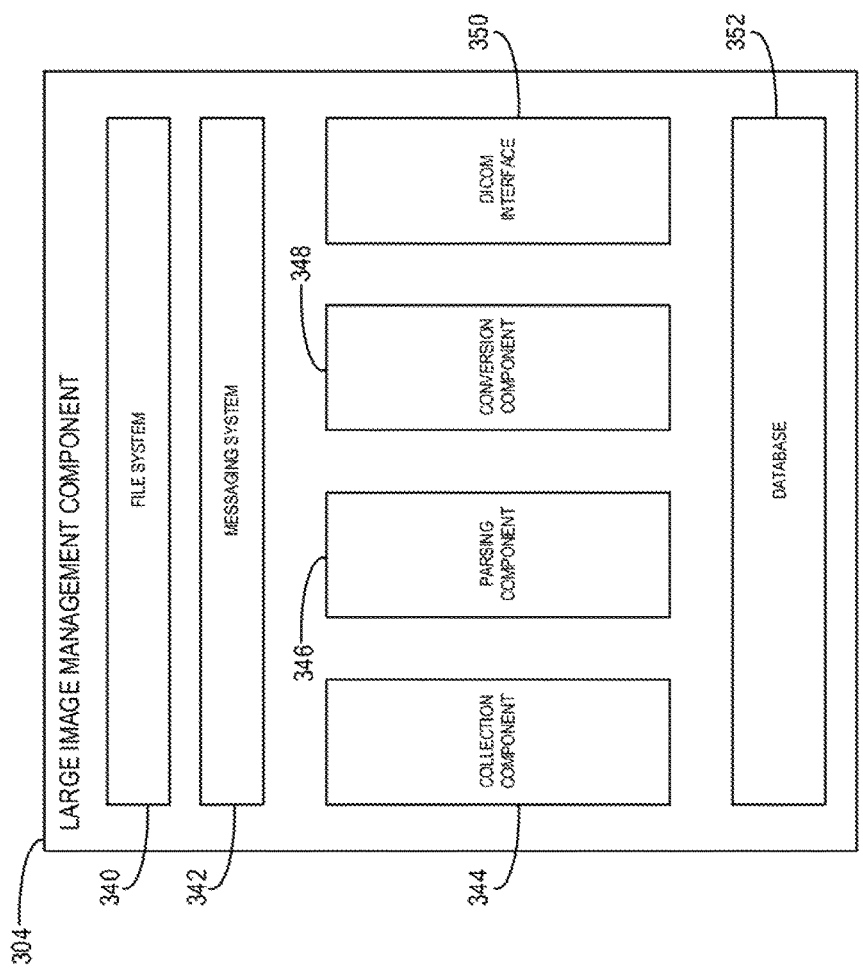
FIG. 3 is a block diagram of large image manager component in accordance with an example embodiment.

An example embodiment of a LIM 304 that may be used to implement LIM 104 is shown in FIG. 3 and described in further detail below. In general, LIM 104 includes a combination of hardware and software components that can be used to manage large medical image data items for example as described below with reference to FIG. 3. The LIM 104 can also include an internal workflow activation component similar to the workflow activation component 114 of the PACS 106. The workflow activation component of the LIM 104 may define workflows specific to the LIM 104, such as workflows relating to processing medical image data items and/or generating representative objects. In some cases, the workflows defined by workflow activation component 114 of PACS 106 may be more general system/enterprise wide workflows while the LIM-specific workflows may be more focused on storage and processing of medical image data items. The LIM 104 workflows may also be triggered by the PACS 106 workflows.

The LIM 104 may include external communication interfaces to interface with external components such as PACS 106, viewer 108, imagers 110, and/or the information storage system 112. The interfaces in LIM 104 may include a variety of APIs configured to communicate using different communication protocols and with different data formats to permit the LIM 104 to interface with various external systems. For instance, the LIM 104 may include a DICOM interface to interface with the PACS 106 in accordance with the protocol used by PACS 106.

In some embodiments, the LIM 104 and PACS 106 may operate in a combined or interdependent manner to provide imager manager 102. The LIM 104 can store the medical image data items and generate representative objects from the stored medical image data items. The representative objects can then be used in the image management workflows of the PACS 106. The PACS 106 may then only request the full medical image data items or full-size pixel data from those medical image data items when requested by a user.

In general, the LIM 104 may store all the medical image data items to facilitate data management by removing large medical image data items from the storage and management workflows of the PACS 106. As well, the LIM 104 can store medical image data items generated in different formats that may not be compatible with the PACS 106 workflows. The LIM 104 can then generate the representative objects as DICOM files that can be managed by the core components of the PACS 106.

The LIM 104 can generate the representative objects with a reduced or limited data size. In some cases, the LIM 104 may generate representative overview objects with a maximum data size of 10 MB that can be transmitted to PACS 106 and used in the PACS 106 management workflows. In some cases, the LIM 104 may generate representative metadata objects with a maximum data size of 5 MB or even 1

MB that can then be send to PACS 106 and used in management workflows. The overview objects may be larger as they can include overview pixel data that may be reviewed by users, while the representative metadata objects may only include metadata used by the management workflows and potentially reviewed by users. The maximum data size of the overview objects and/or representative metadata objects may vary depending on the particular system implementation.

Alternatively, the LIM 104 may manage and store large medical image data items while the PACS 106 stores small medical image data items. The distinction between small medical image data items (i.e. those stored in PACS 106) and large medical image data items (i.e. those stored in LIM 104) may generally be determined based on the data size or expected data size of medical image data items being stored. For example, a threshold data size may be defined by image manager 102 to differentiate between small medical image data items and large medical image data items. Medical image data items greater than or equal to the threshold data size may be determined to be large medical image data items.

The threshold data size may depend on various factors related to particular implementations of system 100. For example, the threshold data size may be defined as 10 GB, 25 GB, 50 GB, or 100 GB in different implementation examples.

In some cases, an expected data size of the medical image data items being stored may be used to differentiate between small medical image data items and large medical image data items. In some cases, the type of medical image data item being stored (e.g. X-Ray, endoscopy video, CT scan) or the imager that generated a particular medical image data item may be used to determine whether to store the medical image data item in the LIM 104 or PACS 106. For example, imagers or image types that tend to generate medical images with larger data sizes may be allocated to the LIM 104 while other medical image data items are allocated to PACS 106. Again, the threshold expected data size (and corresponding image types or imagers) may vary depending on the implementation.

The LIM 104 may perform various operations related to the collection, storage, and processing of medical image data items. The PACS 106 can store representative objects and may perform various operations related to the collection and processing of those representative objects. In some cases the PACS 106 may also store and perform operations related to the collection and processing of small medical image data items, for instance medical image data items already stored in a PACS 106 prior to the addition of the LIM 104. The PACS 106 may also manage the lifecycle and access to both small medical image data items and large medical image data items. This may facilitate integration of the LIM 104 into existing clinical workflows and clinical procedures.

The image manager 102 can be communicatively coupled to one or more viewers 108. The viewers 108 may be computing devices operated by users, such as clinicians, to request, review, and/or analyze medical images among other functions. Users may interact with the image manager 102 through viewers 108.

The large image manager component 104 may facilitate interactions with PACS 106 by removing the large medical image data items from the core workflows of the PACS 106. This may reduce the bandwidth requirements on the core PACS 106 components, and in turn facilitate user interactions with the PACS 106. At the same time, requests for large medical image data items transmitted to the PACS 106 can be re-routed to the LIM 104 to serve the requested medical image to a viewer 108.

From the perspective of a clinician, interactions with the PACS 106 to request and review images may appear the same. However, clinicians may be provided with access to an increased number and type of medical image data item. As well, since the throughput required for the PACS 106 to perform its image management operations may be reduced, clinicians may experience reduced latency when interacting with image manager 102.

As shown by data transmissions 116, 122, and 126 in FIG. 1, the LIM 104 and PACS 106 can operate with two-way communication to manage medical image data items. For instance, the LIM 104 may transmit a metadata message 116 to the PACS 106 indicating that a new medical image data item has been stored in LIM 104 and is available to be accessed. Metadata message 116 or another message sent by LIM 104 may also include one or more representative object corresponding to the new medical image data item. The representative objects may then be used by PACS 106 in image management workflows.

The PACS 106 may determine that one of the medical image data items stored on the LIM 104 should be modified and/or updated and/or archived and/or deleted and/or prefetched and/or processed etc. The PACS 106 may then transmit a management message 126 to the LIM 104 indicating the appropriate lifecycle action. The LIM 104 may then perform a corresponding lifecycle action in relation to the medical image data item identified by message 126.

The image manager 102 may also communicate with one or more viewers 108. The viewers 108 may correspond to reviewing stations usable to receive and display medical images and sub-images. The viewer 108 and PACS 106 may exchange viewer messages 118 relating to medical image data items stored in PACS 106 and/or LIM 104. The viewer 108 may be configured to communicate using the DICOM protocol used by PACS 106.

In some cases, the viewer 108 may provide a request 120 for a medical image to PACS 106. For instance, a user of viewer 108 may select a medical image to request based on data received in the viewer messages 118. If the PACS 106 determines that the request corresponds to a representative object (or in some cases a medical image data item) stored in the PACS 106, the PACS 106 can provide the requested pixel data directly. However, if the PACS 106 determines that the requested medical image corresponds to one of the medical image data items stored in the LIM 104, the request can be re-routed to the LIM 104.

In some cases, a re-routed request 122 may be sent to LIM 104 automatically by the PACS 106 in response to request 120. Alternatively, the PACS 106 may respond to the viewer 108 with an indication that a re-routed request is required. The viewer 108 may then transmit the re-routed request 122 to the LIM 104.

In response to receiving the re-routed request 122, the LIM 104 can identify the pixel data of the requested medical image. The LIM 104 can then transmit an image response message 124 to the viewer 108 that includes the requested pixel data. The image response message 124 may be sent directly to viewer 108, or may be routed through PACS 106. The viewer 108 can then display the pixel data to the user.

The image manager 102 can be communicatively coupled to one or more imagers 110. The imagers 110 can be configured to generate digital medical images in the form of medical image data items. Examples of imagers 110 include digital pathology scanners, endoscopy video cameras, X-Ray scanners, CT scanners, ultrasound scanners, magnetic resonance imagers etc.

In some cases, the image manager 102 may not be directly connected to imagers 110. For instance, the image manager 102 may retrieve medical image data items from image storage components (i.e. storage memory used to store medical image data items) or archives that in turn receive medical image data items from the imagers 110. Image manager 102 may also receive medical image data items from external image management systems, such as those associated with a different healthcare facility.

Information storage system 112 may store additional data associated with medical image data items generated by imagers 110 or stored by image manager 102. Examples of information storage systems 112 include hospital information systems (HIS), Laboratory/Departmental Information Systems (LIS), and/or Radiology Information Systems (RIS).

The image manager 102 may communicate with information storage system 112 to retrieve additional metadata related to medical image data items stored by LIM 104 and/or PACS 106. For example, the image manager 102 may communicate with the information storage system 112 to retrieve patient data associated with a particular medical image data item. The patient data may then be stored as part of the image metadata for the medical image data item.

Referring now to FIG. 2, shown therein is an example of an image management system 200 that includes a PACS 206 without a large image manager component, such as the LIM 104 shown in FIG. 1. An example of a picture archiving and communication system that may be used to implement PACS 206 and its core components is described in detail in U.S. Pat. No. 6,574,629.

In general, the PACS 206 is implemented as a combination of hardware and software components including a processor, volatile memory, non-volatile storage memory, and a communication interface. The communication interface may be one or more data network interfaces, such as an IEEE 802.3 or IEEE 802.11 interface, for communication over a network.

As shown in FIG. 2, the PACS 206 is communicatively coupled to a viewer 208, an information storage system 212 and an image archive 230. The PACS 206 may be directly linked to any one or more of the viewer 208, an information storage system 212 and image archive 230, for example, via a Universal Serial Bus, Bluetooth™ or Ethernet connection. Alternatively, PACS 206 may be linked to any one or more of the viewer 208, an information storage system 212 and image archive 230, via a data communication network or, in some cases, the Internet.

In general, the PACS 206 operates using a defined communication protocol, in this example DICOM. The data stored by the PACS 106 is communicated and managed in accordance with the DICOM standard protocol. For instance, workflows defined by the workflow activation component 214 operate in accordance with the DICOM standard.

The PACS 206 may also include external interfaces or gateways to interface with external components such as the viewer 208, an information storage system 212 and image archive 230. The external interfaces may be configured to receive and transmit data and messages in accordance with defined communication protocols such as DICOM, HL7, FHIR, etc.

The PACS 206 includes a workflow activation component 214 and a database 232. The database 232 may be stored in the non-voltage storage memory of the PACS 206. In some example embodiments, database 232 is a relational database. In other embodiments, database 232 may be a non-relational database, such as a key-value database, NoSQL database, or the like.

The database 232 may be used to store medical image data items. The database can also store other data related to the medical image data items and management of medical image data items. For instance, the database 232 may also store system configuration files that define the workflows used by workflow activation component 214, or workflow settings. The workflow activation component 214 may be generally analogous to workflow activation component 114. However, the workflow activation component 214 may also include workflows relating to the storage of medical image data items for the PACS 206 for implementation without a LIM to store medical image data items.

The viewer 208 and information storage system 212 may generally correspond to viewer 108 and information storage system 112 shown in FIG. 1.

Image archive 230 can include a storage memory. The image archive 230 may provide for long-term persistent storage of medical image data items. Although shown separately from database 232, in some cases the image archive 230 may be stored in database 232. Alternatively, the image archive 230 may be located remotely from the PACS 206.

In the image management system 200 of FIG. 2 the PACS 206 stores and manages all the medical image data items that are accessible via the PACS 206. The PACS 206 may not be able to access or manage medical image data items generated in formats that are not compatible with the defined communication protocol used by the PACS 206. As a result, a user accessing the PACS 206 through viewer 208 may only be shown medical image data items generated in a DICOM format.

As well, the PACS 206 manages all the medical image data items regardless of data size. The workflows defined by workflow activation component 214 may operate the same regardless of the size of a medical image data item. Thus, the determination of whether to process a medical image data item or to modify or move a stored medical image data item may not take into account the data size of the medical image data item involved.

Accordingly, when the PACS 206 workflows indicate that a medical image data item is to be transferred from the database 232 to image archive 230, or vice versa, this may occupy, wholly or partially, the processor and memory of the PACS 206 for the duration of the data transfer. This may cause significant delays or bottlenecks when large medical image data items, sometimes as large as 100s of Gigabytes or even 10s or 100s of Terabytes, are being transferred. Similarly, various other operations on large image data items may occupy significant bandwidth available to PACS 206.

In contrast, in the image management system 100 shown in FIG. 1, medical image data items are stored in the LIM 104. Smaller representative objects corresponding to these medical image data items are provided to the PACS 106 to be incorporated into the workflows. Thus, with little to no modifications to the PACS workflows, the processing and management of large medical image data items can be removed from the PACS 206. This may alleviate strain on the PACS 206 as it manages the lifecycle of both small and large medical image data items.

Referring now to FIG. 3, shown therein is a block diagram of a large image manager component 304 in accordance with an example embodiment. Large image manager component 304 is an example of a large image manager component that may be used as LIM 104 in image manager 102.

The LIM 304 generally includes at least one processor as well as volatile memory and non-voltage storage memory. The processor of LIM 304 may be configured to perform various functions in an image management system in relation to large medical image data items. These functions may be functions that would otherwise be performed by PACS 106, but are removed from the PACS 106 to alleviate strain and/or because the communication protocols used by the PACS 106 may perform the functions inefficiently.

As shown in FIG. 3, the LIM 304 can maintain its own file system 340 and messaging system 342. The file system 340 and messaging system 342 may be maintained independently from the file system of the PACS 206.

As mentioned, the PACS 106/206 may operate in accordance with a DICOM communication protocol. However, the DICOM communication protocol may be inefficiently structured for storing and managing large files. Accordingly, the file system 340 and messaging system 342 can operate in accordance with alternative communication protocols.

The file system 340 and messaging system 342 of the LIM 104 may be configured to handle greater data throughput as compared to a PACS 106/206. For example, the file system 340 and messaging system 342 of the LIM 104 may be configured to have a data throughput in the 10s of TB or greater per day. In contrast, conventional PACS 206 may be configured to have a throughput of only 10s of TB per year. The file system 340 and messaging system 342 of the LIM 104 may be configured to process medical image data items.

The LIM 304 also includes a database 352. The database 352 may be stored in the non-volatile storage memory of the LIM 304. The database 352 can be used to store large medical image data items. In some cases, non-volatile storage memory of the LIM 304 may store pixel objects generated from the large medical image data items. In some cases, non-volatile storage memory of the LIM 304 may store pixel objects generated from the large medical image data items.

The LIM 304 can also include a collection component or collector 344. The collector 344 may communicate with external storage components, such as imagers 110 and/or remote storage memory to collect medical image data items for storage in database 352. In some cases, the collector 344 may also communicate with information storage systems 112 to reconcile additional information with the medical image data items stored in database 352.

Figure 6:
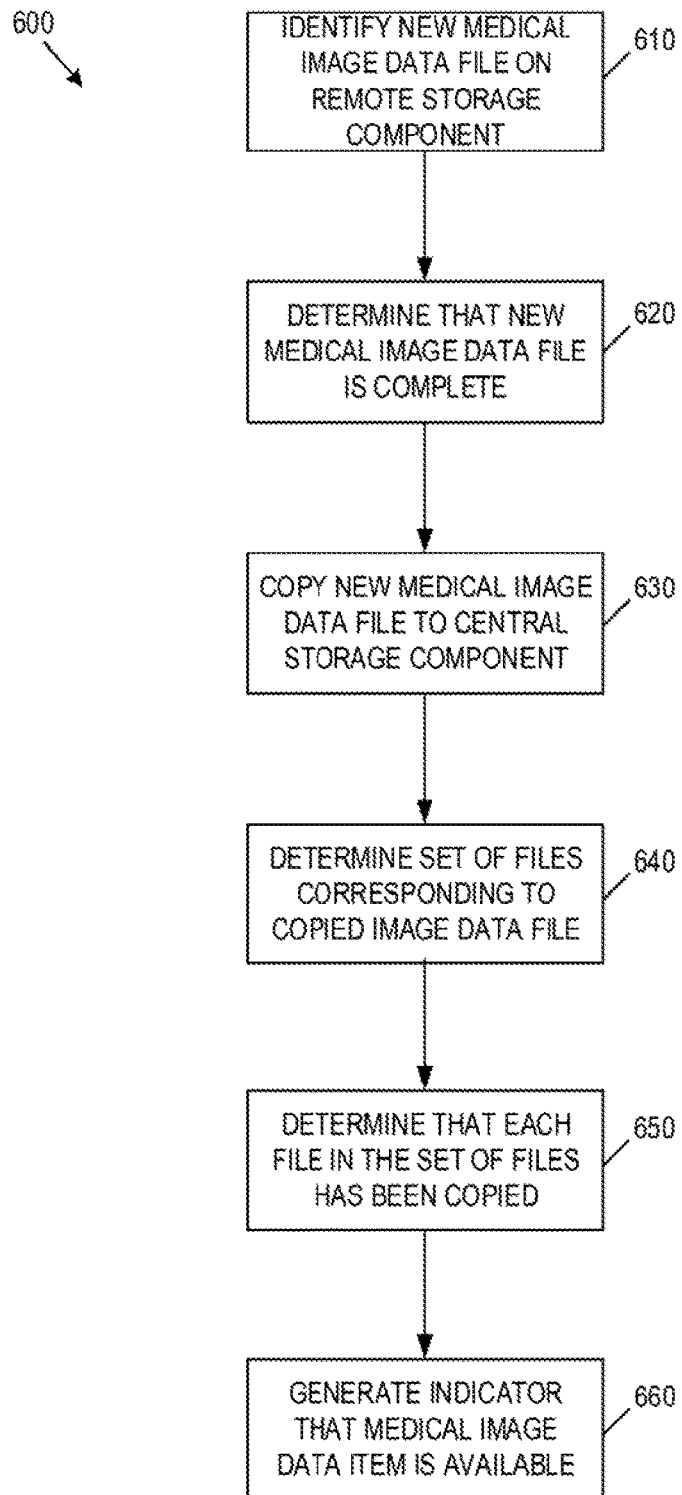
FIG. 6 is a flowchart illustrating a method of collecting medical image data items in accordance with an example embodiment.

In general, the collector 344 may be configured to collect images from external image storage components in various manners. For instance, the collector 344 may replicate medical image data items stored on remote storage memory. The collector 344 may be implemented as a collector application stored on the memory of the LIM 304. An example of an image collection process 600 that may be implemented by collector 344 is shown in FIG. 6 and will be discussed in further detail.

The LIM 304 can also include a parsing component or parser 346. The parser 346 may analyze the medical image data items stored in the database 352 to identify image metadata and image pixel data. The parser 346 may be implemented as a parsing application stored on the memory of the LIM 304.

The LIM 304 may receive or collect medical image data items in various different formats from external image storage components. Examples of received data formats may include proprietary formats; proprietary formats based on open-source formats such as TIFF, JPEG, BMP, as well as DICOM-formatted medical image data items.

The parser 346 may identify the format of the received medical image data items. Based on the format of the received medical image data items, the parser 346 may identify the medical image data files and the portions of medical image data files storing the image metadata and image pixel data respectively. The parser 346 may then extract the image metadata and image pixel data from the analyzed medical image data items. The parser 346 may also store the image pixel data to facilitate retrieval for requests received from the PACS 106 or viewers 108.

The parser 346 can read and extract the metadata stored in the received medical image data items. The parser 346 may store the extracted metadata in a cache storage component to facilitate generating the representative objects. The extracted metadata can then be used e.g. by converter 348 to generate representative objects in a DICOM-compatible format. The parser 346 may store the extracted metadata in a cache storage component to facilitate generating the representative objects.

The parser 346 may also process the pixel data and metadata of the received medical image data items. The parser 346 may generate additional image metadata based on the processing of the received medical image data item. This additional metadata can then be used when generating the representative objects. For example, the parser 346 may analyze the pixel data corresponding to one or more sub-images of the medical image data item to identify sub-image metadata that can be included as part of the additional image metadata.

Figure 7:
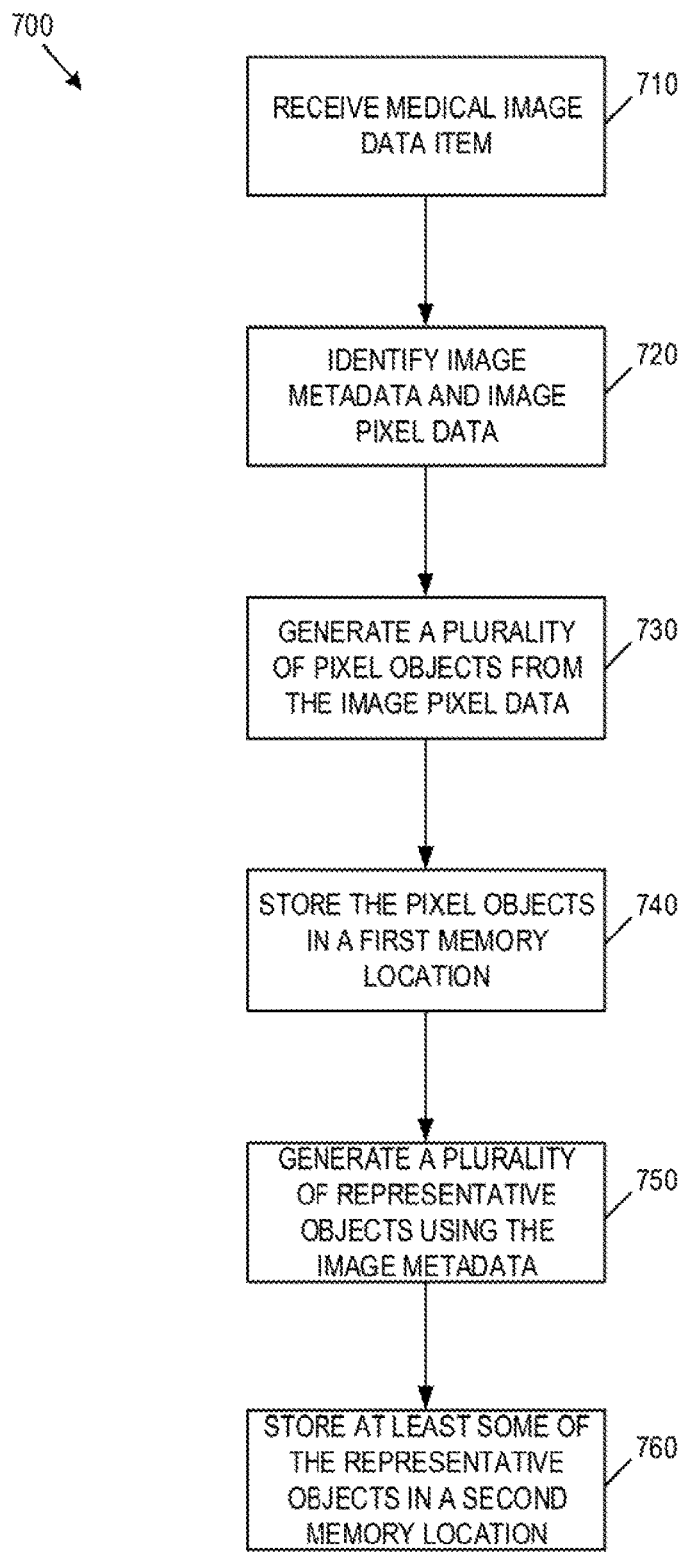
FIG. 7 is a flowchart illustrating a method of processing a medical image data item in accordance with an example embodiment.

The LIM 304 can also include a conversion component or converter 348. The converter 348 may generate various objects corresponding to the medical image data items received and/or stored by LIM 304. For example, the converter 348 may use the extracted image metadata and/or extracted image pixel data from the parser to generate objects corresponding to the medical image data items received and/or stored by LIM 304. The converter 348 may be implemented as a conversion application stored on the memory of the LIM 304. An example of an image conversion process 700 that may be implemented by converter 348 is shown in FIG. 7 and will be discussed in further detail.

In general, the converter 348 may generate pixel objects corresponding to the medical images and/or sub-images of a medical image data item. The pixel objects can be generated from the image pixel data extracted by parser 346. In some cases, the converter 348 may also generate pixel metadata objects defining characteristics of the pixel objects and spatial relationships between the pixel objects.

The converter 348 may generate representative objects corresponding to the medical images and/or sub-image of the medical image data item. Some of the representative objects may be provided to the PACS 106 to be used as part of the PACS 106 workflows. The converter 348 may generate some of the representative objects in a DICOM-compatible format to permit easy integration with the PACS 106 workflows. Examples of representative objects can include representative metadata objects and overview objects. The converter 348 may also generate the representative objects with a limited maximum data size to minimize the size of the data objects incorporated into the PACS 106 workflows.

The LIM 304 can also include a DICOM interface 350. The DICOM interface may provide an interface or API between the LIM 304 and PACS 106. The DICOM interface 350 can be configured to communicate with the PACS 106 to transmit and receive DICOM-compatible data, such as messages 116, 122 and 126 shown in FIG. 1. The DICOM interface 350 may be used to transmit DICOM-compatible representative objects to the PACS 106.

The DICOM interface 350 may also communicate with a viewer 108 that is configured to operate according to the DICOM protocol. The DICOM interface 350 may receive re-routed requests 122 from the PACS 106 and/or viewer 108. The DICOM interface 350 may then transmit pixel data or pixel objects to the viewer 108 in a format that is DICOM compatible or otherwise usable by viewer 108.

The database 352 may also store information related to the large medical image data items, such as unique file identifiers and unique set identifiers corresponding to medical image data files and sets of medical image data files respectively. The database 352 may also include an index or address book that correlates the unique file identifiers and/or unique set identifiers with the memory addresses of the corresponding medical image data files or sets of medical image data files. The database 352 may also indicate whether particular medical image data items are available for access by viewer 108 and/or whether medical image data items are available for further processing e.g. by parser 346.

In some cases, the non-volatile memory of LIM 304 (e.g. database 352) may include both a long-term storage section and a short-term access section or cache section. The long-term storage section may provide permanent or effectively permanent storage for medical image data items. In some cases, the long-term storage component may be located remotely from the processor of the LIM 304, for instance as an off-site or cloud storage memory. This may allow for flexibility and scaling as additional medical image data items (and thus increasing amounts of data) are stored in the LIM 304.

The cache storage may be used to store medical image data items and/or medical image data files in a manner that is more readily accessible for communication with PACS 106 and/or viewer 108. For instance, the cache storage may be used to store objects derived from the medical image data items or individual files from the medical image data items. The cache storage may store medical image data files or objects that have been requested (e.g. by a viewer 108 and/or external system) or are expected to be requested (e.g. as a result of a pre-fetch messages from a PACS 106). The data stored in the cache storage may be stored in a format compatible with the system requesting or expected to request the object or file. This may provide a more rapid response to requests from the viewers 108 or PACS 106.

The cache storage may have a reduced storage capacity as compared to the long-term storage component. Accordingly, objects or files stored in the cache storage may be stored for a limited time period (or until additional capacity is required). In some cases, objects or files may be stored in the cache storage in response to requests or pre-fetch messages.

In some cases, the medical image data items received by LIM 304 may be stored in their originally received or "as-is" format. This may ensure data fidelity for the medical image data items being stored. In some cases, there may also be regulatory requirements mandating the storage of the medical image data items in their original format. The original medical image data items may be stored in the long-term storage section.

The LIM 304 may also process the medical image data items to generate pixel objects and other representative objects. In some cases, the LIM 304 may store these pixel objects and/or representative objects in addition to the original medical image data items. This may allow individual medical images or sub-images (and/or related metadata) to be easily provided in response to requests from PACS 106 and/or viewer 108.

Alternatively, the pixel objects and/or representative objects may be generated in response to requests (or anticipated requests/pre-fetch instructions from PACS 106) from viewers 108. The pixel objects and/or representative objects may then be stored temporarily e.g. for the time period during which they are expected to be requested.

In some cases, the cache storage may be used to store the pixel objects and/or representative objects. In this way, the cache storage can be used to store files that include data expected to be requested by PACS 106 and/or viewer 108. The cache storage may then omit other portions of the medical image data items that are unlikely to be requested, or that are otherwise stored in the PACS 106 (such as by representative objects already transmitted to the PACS 106).

The LIM 304 can also include an internal workflow activation component similar to the workflow activation component 114 of the PACS 106. The workflow activation component of the LIM 304 may define workflows specific to the LIM 304, such as workflows relating to processing medical image data items and/or generating representative objects. The LIM 304 may also include cache management workflows that define how and when to store objects in the cache storage and how and when to remove or delete objects from the cache storage.

The workflows defined by the LIM 304 may be triggered by workflows defined by the PACS 106/206. For example, the PACS 106 may define cache management workflows that trigger the corresponding cache management workflows of the LIM 304. The PACS 106 may transmit a pre-fetch message to LIM 304 to trigger the corresponding cache management workflow.

Figure 4:
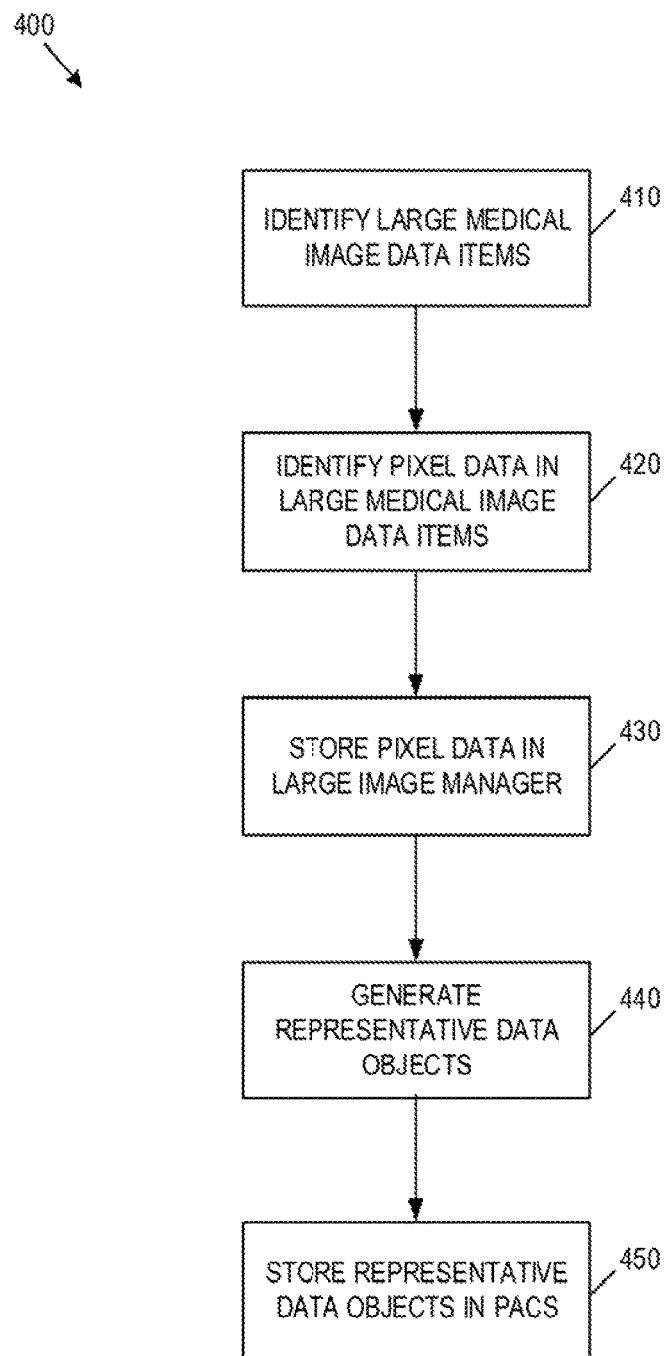
FIG. 4 is a flowchart illustrating a method of managing large medical images in accordance with an example embodiment.

Referring now to FIG. 4, shown therein is a flowchart of a method 400 for managing medical images in accordance with an example embodiment. In some cases, method 400 may be implemented as an image management application on an image management system such as image manager 102.

At 410, one or more medical image data items are identified. The medical image data items may be identified from a medical imager, such as imagers 110 shown in FIG. 1. The medical image data items may also be identified from other storage locations, such as those associated with imagers 110 or with other external systems. For example, the medical image data items may be identified or received from external image management systems such as image management systems associated with external healthcare facilities. The medical image data items may also be identified from an image archive, such as image archive 230 shown in FIG. 2.

The image manager 102 may be coupled to multiple image storage memory locations. The image manager 102 may identify medical image data items on the storage memory locations. The image manager 102 may transfer or copy the identified medical image data items to a local or central storage memory associated with image manager 102. An example process 600 for identifying and collecting medical image data items is described in further detail below with reference to FIG. 6.

The process of identifying medical image data items may be implemented by either or both of the LIM 104 and PACS 106. In some cases, identifying medical image data items may be incorporated into a general process for identifying and collecting medical image data items. The image manager 102 can determine that one or more of the identified medical image data items are large medical image data items.

In some cases, large medical image data items may be identified from the above-noted storage components or imagers. The identified medical image data items may be compared to large image criteria to determine if the identified medical image data items should be considered large image data items. For instance, a threshold data size may be used to determine whether an identified medical image data item is a large image data item. Alternatively, an image type or data item type may be used to differentiate large medical image data items from small medical image data items (e.g. based on the type of imager or imaging process/format used to generate the image data item).

The large medical image data items may then be stored in (e.g. copied to) LIM 104. For example, the large medical image data items may be stored in database 352 of LIM 304. In some cases, the other identified medical image data items (i.e. small medical image data items) can be stored in the PACS 106. However, all medical image data items may be stored in the LIM 104 in other cases to provide a comprehensive image storage memory.

In some cases, the medical image data items may be stored in the database 352 unprocessed. Alternatively, the medical image data items may be processed prior to storage. Alternatively, processed and unprocessed versions of the medical image data items may both be stored in LIM 304.

At 420, pixel data can be identified in the medical image data items. The pixel data may be identified in the medical image data items after an original medical image data item is stored on the LIM 104/304. Alternatively, the pixel data may be identified in a medical image data item prior to storage on the LIM 104. This may allow the LIM 104 to extract the pixel data from the medical image data item prior to storage.

The pixel data may be identified by the image manager 102 identifying the medical image data files in the medical image data item that include pixel data for the medical image and sub-images of that image data item. In some cases, a sub-set of the medical image data files may be identified as pixel files that include the pixel data.

In some cases, the image manager 102 may identify portions of the medical image data files that include the pixel data for the medical image data item. For instance, some of the medical image data files may include both image metadata and image pixel data relating to the medical image and/or a sub-image of the medical image. The pixel data portions of the medical image data files that include the image pixel data can be identified as defining the pixel data.

The pixel data may be identified at least partially based on a format of the medical image data item. For instance, the format of the medical image data item may indicate that one or more of the medical image data files are index files that include metadata relating to the set of medical image data files in the medical image data item. The image manager 102 may parse the index file to identify the medical image data files that include the pixel data.

The image manager 102 may also determine the portions of the medical image data files that include pixel data from file structure definitions for the particular format of the medical image data item. For instance, the format of the medical image data item may specify how data is arranged within a medical image data file. The format may define a particular metadata portion and a particular pixel portion. The pixel data may then be identified in the particular pixel portion of the medical image data files. In some cases, the index file may additionally or alternatively identify the particular pixel portion of one or more medical image data files.

At 430, the pixel data can be stored in a storage memory of the large imager manager 104. In some cases, storing the pixel data may refer to the storage of the medical image data item itself which includes the pixel data identified at 420. For instance, the medical image data item may be stored in its original format and state (or at least the format in which it was received and/or collected by image manager 102).

Additionally or alternatively, the pixel data may be extracted from the medical image data item and stored in the storage component as pixel objects. In some cases, the pixel data may be extracted from the medical image data items prior to storage in LIM 104. For example, the pixel data identified at 430 may be used to generate one or more pixel objects for the medical image data item.

The pixel objects may include one or more pixel objects for each sub-image in of the medical image data item. For instance, each sub-image may have a corresponding set of pixel objects stored in the storage memory. When a request is received by LIM 104 for a sub-image or a portion of a sub-image, the LIM 104 may then retrieve the corresponding pixel object or pixel objects. The pixel object(s) may then be provided to fulfill the request. Each pixel object may be stored at an individually addressable memory location in the storage memory to facilitate retrieval of individual pixel objects.

In some cases, the pixel objects may be stored independently in the storage component. That is, the address in memory at which each pixel object is stored may be determined independently from the address location for other pixel objects. This may provide flexibility to store the pixel objects using distributed memory address locations.

In some cases, the set of pixel objects for a sub-image may be stored as a group in the memory. In such cases, each set of pixel objects may then be stored independently of the other sets of pixel objects.

In some cases, both the original medical image data item and the extracted pixel data can be stored in the storage component. This may ensure compliance with regulatory requirements, while permitting direct retrieval of the pixel data for individual sub-images and portions of the sub-images without requiring processing on-the-fly.

In some cases, the original medical image data item may be stored in a long-term storage memory section while the extracted pixel data is stored in a cache section. The cache may provide more rapid access to the data stored therein. Accordingly, the pixel data may be retrieved to fulfill medical image requests received by LIM 104.

Alternatively, only the original medical image data item may be stored permanently. Alternatively, only the extracted pixel data may be stored in the storage component and the original medical image data item can be discarded or stored in a remote image archive.

In some cases, (i.e. when extracted pixel data/pixel objects are not stored permanently), pixel data may be extracted from a medical image data item in response to a request from a viewer 108. Additionally or alternatively, pixel data may be extracted from a medical image data item in response to a pre-fetch message from PACS 106. Additionally or alternatively, the LIM 104 may determine that a request for the pixel data is expected (for instance, because the pixel data/pixel object is related to pixel data/pixel objects recently requested) and extract the pixel data prior to receiving a request.

In such cases, the pixel data may be stored temporarily in the LIM 104 (e.g. in a cache). The pixel data may then be discarded/deleted after a period of time and/or once a storage threshold is reached.

In some cases, the pixel data from the medical image data item may be analyzed to identify additional properties of the sub-images of the medical image data item. These additional sub-image properties may then be stored as additional metadata for the medical image data item. For example, the sub-image properties may be used to provide an indication or estimate of the importance of a particular sub-image or sub-image region.

At 440, the large image manager can generate representative data objects for the medical image data items. The representative objects may be generated to represent the pixel data, and related image metadata, stored in the LIM 104. At 450, at least some of the representative data objects can be stored in a storage memory of the PACS 106.

Some of the representative objects may be generated in a DICOM-compatible format. The DICOM-compatible representative objects may be transmitted from LIM 104 to PACS 106 to be incorporated into the PACS 106 workflows.

The representative objects generated at 440 may include at least one representative metadata object. Each representative metadata object may include metadata that represents or reflects characteristics of one of the sub-images in the medical image data item.

The representative metadata objects may be generated by the LIM 104 in a DICOM-compatible format. The representative metadata objects may be transmitted to PACS 106 and then used by the PACS 106 in image management workflows. For instance, users accessing the PACS 106 may receive data from the representative metadata objects as part of a process for determining what medical image to request and/or requesting medical images.

The representative objects generated at 440 may also include overview objects. The overview objects may be generated using both the pixel data and metadata from the medical image data item. Each overview object may correspond to the medical image and/or a sub-image of the medical image. The overview objects may include pixel data for a sub-sampled or lower resolution representation of a sub-image. The overview objects may also be generated in a DICOM-compatible format and provided to PACS 106.

In some cases, pixel metadata objects or fragments may also be generated. Each pixel metadata object may include metadata relating to a specific pixel object generated from the pixel data of the medical image data item. The pixel metadata objects may include identifying metadata defining characteristics of an individual pixel object. The pixel metadata objects may also include relational metadata defining relationships between the pixel objects. For instance, the relational metadata may identify a spatial relationship between multiple pixel objects.

In some cases, the pixel metadata objects may be stored in the LIM 104. As the pixel objects are also stored in the LIM 104, the pixel metadata objects may not be required unless or until a request is received for one or more pixel object. Accordingly, the pixel metadata objects can be stored in the LIM 104 to reduce the storage required by PACS 106. As with the pixel objects, in some cases the pixel metadata objects may be generated only in response to a request (or expected request or pre-fetch instruction). An example of an image processing method to general pixel object, representative objects, and pixel metadata objects is described in further detail below with reference to FIG. 7.

As mentioned, the pixel objects and representative objects may be generated from metadata and pixel data identified in a medical image data item. In some cases, the metadata and/or pixel data is extracted from the medical image data items and stored, for instance as pixel objects and representative objects.

In some cases, the LIM 104 may store a mapping of the medical image data item indicating the portions of the medical image data items storing metadata and pixel data respectively. For instance, the LIM 104 may store the mapping of the medical image data item in embodiments where the pixel objects are not stored permanently. This may facilitate the subsequent generation of pixel objects and/or representative objects.

By storing the medical image data items in LIM 104 external to the core workflows of the PACS 106, unnecessary transmission or movement of the medical image data items may be avoided because those data items are not directly involved in the workflows. This may prevent network saturation and increase the availability of the PACS 106 for other, potentially critical, functions.

The representative objects provided to PACS 106 can be generated with a limited or restricted maximum data size, such as 1 MB or 10 MB for example. The maximum data size may vary for different types of representative objects. For example, overview objects may have a maximum data size of 10 MB while representative metadata objects may have a maximum data size of 1 MB. However, it should be noted that the maximum data size may vary depending on the particular system implementation.

Figure 5:
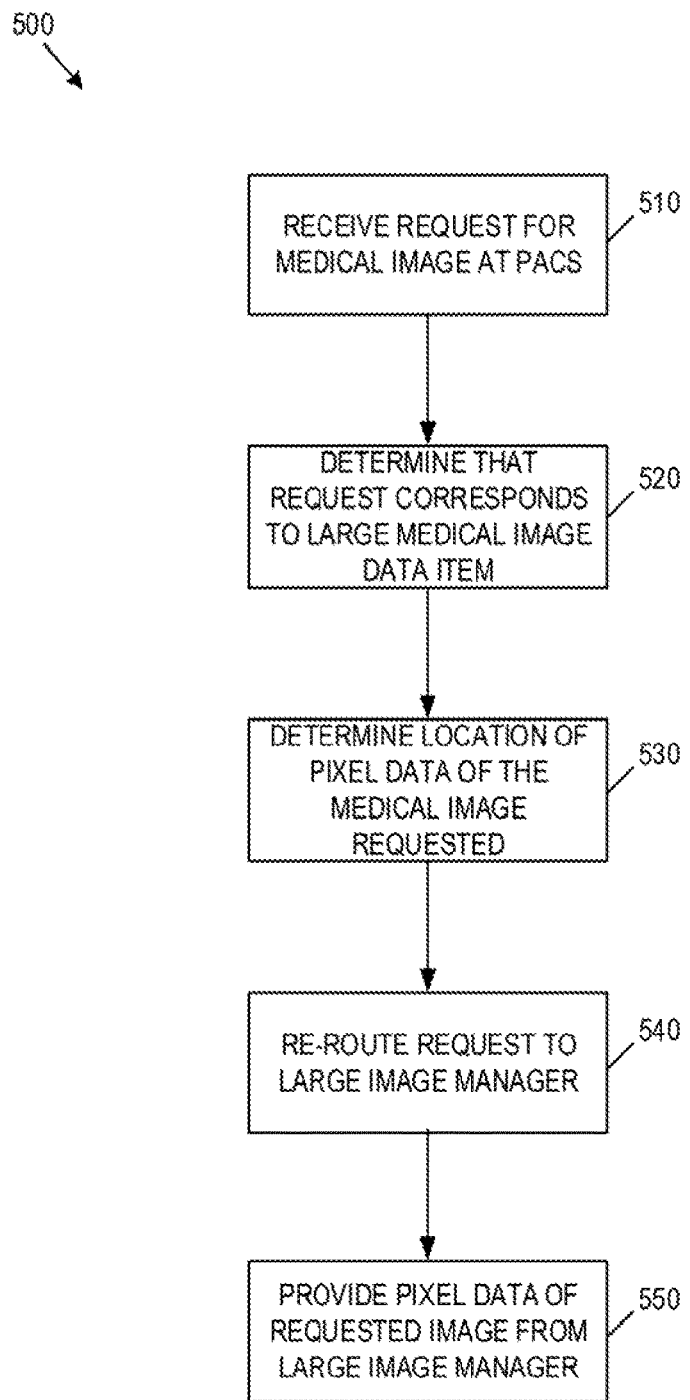
FIG. 5 is a flowchart illustrating a method of providing pixel data for large medical images in accordance with an example embodiment.

Referring now to FIG. 5, shown therein is a flowchart of a method 500 for managing medical images in accordance with an example embodiment. In some cases, method 500 may be implemented as an image management application on an image management system such as image manager 102. In some cases, methods 400 and 500 may both be implemented as part of the same image management application.

Method 500 is an example of a process that can be used to provide pixel data in response to a request for a medical image. The method 500 may be generally implemented as part of a system, such as system 100, in which large medical image data items are stored external to the core component of PACS 106.

At 510, a request for a medical image is received at PACS 106. The medical image can be received from computing device such as viewer 108. A user, such as a clinician, interacting with the viewer 108 may input a request for a sub-image or region of a sub-image to the PACS 106.

The viewer 108 may transmit a request to the PACS 106 for a sub-image or a portion of a sub-image. The request may include a requested image identifier corresponding to the unique identifier of the sub-image and/or sub-image region. The viewer 108 may determine the requested image identifier as part of a series of communications between the viewer 108 and PACS 106.

A user interacting with viewer 108 may initially select one or more representative objects stored on the PACS 106 via a user interface provided by viewer 108. For example, the PACS 106 may transmit one or more metadata representative objects and/or overview objects to the viewer 108 in message 118. In some cases, a user may initially select or identify a particular patient at viewer 108. The PACS 106 may then provide representative objects to the viewer 108 that correspond to the patient. The viewer 108 may then display the metadata representative objects and/or overview objects in a GUI. A user may select one of the representative objects and initiate a request for the corresponding sub-image or sub-image region.

In some cases, the PACS 106 may provide multiple overview objects corresponding to the same sub-image. For example, each of these overview objects may include pixel data for the same sub-image but at a different resolution. A user interacting with viewer 108 may initially review one or more overview objects to perform a preliminary review of the medical image and/or sub-image. If the user determines that a higher resolution version is required, the request may be initiated by a user, for instance by selecting a button in the GUI of viewer 108 to provide the high resolution sub-image and/or sub-image region. The request 120 may then be transmitted to the PACS 106.

At 520, the PACS 106 can determine that the requested medical image corresponds to a medical image data item for which pixel data is stored in the LIM 104. The PACS 106 may determine that the requested medical image corresponds to a medical image data item stored in LIM 104 based on representative objects stored in PACS 106. For instance, the viewer 108 may request the medical image that corresponds to a representative object selected by viewer 108 during the exchange of messages 118. The PACS 106 may determine from metadata in the selected representative object that the medical image is a medical image data item stored in LIM 104.

In some cases, the PACS 106 may determine that the requested image corresponds to a large medical image data item based on the type of image requested. As mentioned, medical image data items may be determined to be large medical image data items based on the type of imager and/or image processing used to generate the image. Accordingly, a request from viewer 108 may indicate a medical image of a particular type. The PACS 106 may then determine that the particular type corresponds to image types defined as large medical image data items.

In some cases, the request from viewer 108 may indicate directly that the requested medical image corresponds to a medical image data item stored in LIM 104. For instance, viewer 108 may determine that the requested medical image is stored in the LIM 104 based on metadata in the messages 118 received from PACS 106. The viewer 108 may then indicate in request 120 that the medical image corresponds to a medical image data item stored in LIM 104 (e.g. by setting a large image flag or bit).

At 530, the location of the pixel data corresponding to the requested medical image can be determined. In various embodiments, the location of the pixel data may be determined by the LIM 104, PACS 106 and/or viewer 108.

In some cases, the address location of the pixel data corresponding to the requested medical image may be included in the metadata of one or more representative objects stored in PACS 106. For example, the representative object(s) may include a URL indicating the location of the pixel data. When the representative object or a corresponding representative object is selected, the address location of the pixel data can be determined directly from the URL.

At 540, the request can be re-routed to the large image manager. Once the PACS 106 has identified that the requested image corresponds to a medial image data item stored in LIM 104, the request can be re-routed to LIM 104. In some cases (e.g. where small medical image data items are stored in the PACS 106), when the PACS 106 determines that the requested image corresponds to a small image data item, the requested image can be provided by PACS 106 directly, e.g. from database 232.

The step of re-routing the request to LIM 104 may occur before or after determining the memory location of the pixel data shown at 530. For instance, the memory location may be identified in a URL used by PACS 106 or viewer 108 to initiate the request. Alternatively, the re-routed request may merely identify the unique identifier of the requested image. In such cases, LIM 104 can determine the memory address location of the requested image based on the unique identifier identified from the re-routed request.

In some cases, the request may be re-routed to LIM 104 via the PACS 106. For instance, the viewer 108 may transmit a request for medical image to the PACS 106 and the PACS 106 may automatically re-route the request to the LIM 104.

In other cases, the viewer 108 itself may re-route the request to the LIM 104. In some cases, the viewer 108 may transmit a request for medical image to the PACS 106, the PACS 106 may respond to viewer 108 with a re-route message indicating that the request should be re-routed to the LIM 104. The viewer 108 may then re-route (i.e. re-transmit) the request to the LIM 104.

In some cases, the viewer 108 may determine based on metadata messages 118 that the medical image to be requested is stored in LIM 104. In such cases, the viewer 108 may automatically re-route its request to the LIM 104 based on the metadata from the representative objects stored in PACS 106.

At 550, the LIM 104 can provide the pixel data of the requested image to the viewer. In some cases, the LIM 104 may transmit the pixel data to the viewer 108 directly. Alternatively, the LIM 104 may transmit the pixel data to the PACS 106 and PACS 106 can in turn provide the pixel data to the viewer 108.

In some cases, the LIM 104 may simply retrieve the pixel data for transmission from pixel data already stored on LIM 104. Alternatively, as mentioned above, the pixel data may be extracted from the corresponding medical image data item in response to the request. In some cases, the LIM 104 may transmit only the pixel data for the request image.

In some cases, the LIM 104 may additionally transmit pixel metadata to the viewer 108. For instance, where the viewer 108 is capable of processing pixel metadata objects indicating the relationship between multiple pixel objects, the LIM 104 may transmit multiple pixel objects and the corresponding pixel metadata objects to the viewer 108. Alternatively, the LIM 104 may only transmit pixel data corresponding to an individual sub-image or sub-image region displayable in the GUI provided by viewer 108.

The viewer 108 may be configured to communicate using the DICOM protocol used by PACS 106. Accordingly, the LIM 104 may generate a response that includes the pixel data in a format that is compatible with the DICOM protocol used by viewer 108.

Collection of Large Image Data Items

The following is a general description of systems and methods for collecting medical image data items and other features set out herein that may be used by itself or in combination with one or more embodiments disclosed herein, including systems and methods for managing medical image data items, systems and methods for processing medical image data items, and systems and methods for transferring medical image data items. The following description contains various features of systems and methods for collecting medical image data items which may be used individually or in any combination or sub-combination.

Collecting medical images from image source locations, such as imagers or storage components associated with imagers, has a number of associated difficulties. Medical image data items are generated in various different formats. Different imagers or imaging software products may each use different image formats to generate medical image data items. This can result in medical image data items with different data structures.

In some cases, the process for generating a medical image data item on an image source location may be unknown to an external system communicating with or accessing the image source location. As well, the file system (e.g. Windows, Linux etc.) may vary across image source locations. As a result, the expected file structure of a medical image data item may not be immediately apparent.

As well, medical image data items are increasing in size. This can result in complex data structures as a medical image data item may be stored in multiple medical image data files. The process of creating the medical image data files for a single medical image data item may also be a lengthy and time-consuming process. Accordingly, it may be difficult to ascertain when an item has finished being generated.

It may also be impractical or impossible to execute any processes on the image source location. For instance, a central system that is configured to collect medical image data items may be limited to performing read operations on the image source location. This may make the process of collecting medical data items more unpredictable, as the image collection system does not have any control over how and when medical image data items are generated, modified, stored, moved and/or deleted.

The image source location may also have data management processes that complicate the process of collecting medical image data items. For instance, the file names given to medical image data files or medical image data items on an image source location may be repeated over time. An image source location may routinely delete items from its image storage memory after a period of time (e.g. upon reaching a storage capacity threshold) and then re-use the same file names once previously stored items have been deleted. As well, in some cases the metadata (e.g. timestamps) included in medical image data items may be unreliable or incorrect. Accordingly, an image collection system may not be able to rely on file names or timestamps to identify distinct medical image data items.

Embodiments of image collection systems and methods described herein may allow medical image data items to be collected from various different image source locations. Embodiments described herein may facilitate the acquisition of medical image data items from isolated and distributed image source locations, such as medical imagers. This may allow for centralized storage and/or management of a broader selection of medical image data items. Embodiments described herein may also provide flexible image collection processes that are configured to interact with, and collect images from, different types of image source locations.

Some embodiments described herein provide systems and methods for collecting medical image data items from one or more remote image storage devices or remote storage memory. In some cases, the systems and methods for collecting medical image data items may be used with systems and methods for managing medical image data items described herein.

In some cases, the remote storage memory or remote image storage memory may be provided by medical imagers. In some cases, the remote storage memory may also include other storage components such as medical image archives. The remote image storage memory may store medical image data files generated in various data formats.

In some cases, the remote storage memory may not permit the LIM, PACS or other external image collection systems to create or modify any of the data or files stored thereon. Accordingly, the image collection system may be limited to monitoring/observing the data generated and stored on the remote storage memory and collecting/copying that data.

The image collection system may define unique file identifiers for medical image data files identified on the remote storage memory. The unique file identifiers may be independent of file characteristic metadata assigned to the data files on the remote storage memory.

The image collection system may also define sets or expected sets of files corresponding to a medical image data item. Each set of files may also be assigned a unique set identifier. The unique set identifier may include the unique file identifiers assigned to each file or expected file for that set. The image collection system can use the unique file identifiers and unique set identifiers to ensure that a medical image data item is completely collected. This also allows the image collection system to independently identify the collected files, as the identifiers can remain independent of any deletions or modifications to files stored on the remote storage components.

As individual medical image data files may be large in size, there may be a delay between the time a new file is identified and when it has finished being generated or stored on the remote storage memory. Accordingly, prior to copying a medical image data file from the remote storage memory, the image collection system may determine that storage of the medical image data file on the remote storage memory has completed. The image collection system may monitor the file characteristics of the medical image data files on the remote storage memory to determine whether storage has been completed.

The image collection system may also monitor collection of the individual files that form the set of medical image data files that define a medical image data item. Once all of the medical image data files in the medical image data item are copied by the image collection system, the image collection system may generate an indicator that the medical image data item is available. This indication may be used to initiate further processing, or to indicate that the medical image data item can be retrieved or provided in response to a request.

The image collection system may also have various defined image collection criteria such as image collection paths, image priority criteria, security credential criteria, numbers of re-try, image destination criteria. The image collection criteria may include both user-defined and system defined collection criteria.

Referring now to FIG. 6, shown therein is a flowchart of a method 600 for collecting medical image data items in accordance with an example embodiment. In general, method 600 may be used by a central image collection system to collect medical image data items from remote image storage memory associated with various image source locations. In some cases, method 600 may be implemented as an image collection application that forms part of an image management system such as image manager 102.

A central processor may be communicatively coupled to a plurality of remote image storage memory instances or components to collect medical image data items from different storage locations. The central processor may communicate with each remote image storage memory component to identify medical image data files.

In some cases, the central processor may be limited to read operations on one or more of the remote image storage memory components with which it communicates. That is, the central processor may not be able to perform any operations or modifications to the data stored on the remote image storage memory components. The central processor may be limited to observing and copying data from the remote image storage memory components.

At 610, a new medical image data file can be identified on a remote image storage memory. In some cases, the remote image storage memory can be a medical imager or storage memory associated with a medical imager. In other cases, the remote image storage memory may be an image archive or part of an external image management system.

The central processor may identify a set of image data files stored on the remote image storage memory. The central processor may then identify the new medical image data files from the set of image data files stored on the remote image storage memory. An example process for identifying new medical image data files is shown in Table 1:

TABLE 1

Example Process for Identifying New Medical Image Data File

| Step | Action |
|---|---|
| 1 | Identify unique identifiers of a set of images at the image source location/remote image storage memory; |
| 2 | Store the unique identifiers of copied images in a database on the central storage memory; |
| 3 | Identify remote file identifiers for a subsequent read of the set of images at the image source location; |
| 4 | Compare result of Step 3 against unique identifiers stored in central storage memory (e.g. at Step 2) |
| 5 | Determine a list of potential new file identifiers from the comparison at step 4 (i.e. file identifiers identified at step 3 not yet stored in the central storage memory) |
| 5 | Process potential new file identifiers to identify new file identifiers. |
| 6 | Update a DetectedFileQueue to add new file identifiers |
| 7 | Return to Step 3 |

The central processor may assign each image data file a unique file identifier. The central processor may associate the unique file identifier with the file characteristics or properties of the image data file. For instance, each unique file identifier may be associated with a particular combination of file characteristics such as file name, timestamp, format, file size and the like. In some cases, certain initially variable file characteristics associated with a unique file identifier may be updated until the central processor determines that storage of the image data file on the remote image storage memory component has completed (e.g. to account for changes in file size as the image data file is being created).

The unique file identifier can be defined by the central processor independently of the file characteristics of the image data file. For example, the unique file identifier may be independent of the file name and timestamp of the image data file on the remote image storage memory. This may ensure that the central processor can uniquely identify the different medical image files being stored on the remote image storage memory component, for instance in cases where the remote image storage memory component re-uses file names over time or may generate unreliable metadata (e.g. incorrect time stamps).

The central processor may then compare the unique file identifiers for the image data files on the remote image storage memory component to unique file identifiers stored in a local/central storage memory associated with the central processor. The unique file identifiers stored on the local/central storage memory may correspond to medical image data files already stored in the local/central storage memory. New file identifiers may then be determined based on the comparison.

In some cases, the central processor may monitor the remote image storage memory locations and identify when additional files are stored on the remote image storage memory. For instance, changes to the set of image data files (e.g. file without previously assigned unique identifiers) may indicate that additional files have been stored. The additional files may then be identified as new medical image data files.

The central processor may monitor each remote image storage memory location on a continual (i.e. ongoing) basis. For example, the central processor may monitor each remote image storage memory location at periodic intervals to determine if any new medical image data files have been stored. When a new medical image data file is identified, the central processor may assign that new medical image data file (i.e. its unique identifier) to a new file set. The new file set may include a plurality of medical image data files that are to be copied. The new file set can be used to order the medical image data files that to be copied to the central storage memory.

In general, the new file set may be implemented in various configurations to allow the medical image data files in the new file set to be arranged in a particular order. For example, the new file set may be implemented as a queue (e.g. a messaging queue), such as DetectedFileQueue shown in Table 1. Alternatively, the new file set may be ordered using a database table or other configuration known to a person skilled in the art.

The new file set may also be used to ensure that medical image data files have finished being generated at the remote storage memory prior to being copied to the local/central storage memory.

At 620, the central processor can determine that the new medical image data file is complete at the remote image storage memory. The central processor may determine that a file is complete when the medical image data file has finished being generated on the remote image storage memory.

As medical image data files may be large in size, generating a medical image data file may occur over a period of time. As a result, the medical image data file may still be in the process of being generated when it is identified by the central processor at 620. Accordingly, the central processor may monitor the file characteristics of new medical image data files to ensure that the file has completed being stored/generated on the remote image storage memory prior to being copied. An example process for identifying completed medical image data files is shown in Table 2:

TABLE 2

Example Process for Identifying Completed Medical Image Data Files

| Step | Action |
|---|---|
| 1 | Read/Receive next available file/file identifier from DetectedFileQueue |
| 2 | Read file characteristics of file at the source location |

TABLE 2-continued

Example Process for Identifying Completed
Medical Image Data Files

| Step | Action |
|---|---|
| 3 | Compare file characteristic values from Step 2 against values associated with file identifier stored in DetectedFileQueue (based on the vendor/scanner specific policy retrieved). |
| 4 | If change detected at Step 3, update file characteristic values in DetectedFileQueue and Return to Step 1. |
| 5 | If no change detected at Step 3, compare file characteristic values to expected complete set of file characteristics. |
| 6 | If file characteristic values match expected complete set, move file identifier from DetectedFileQueue to CompletedFileQueue. |
| 7 | Return to step 1 |

As mentioned, the new medical image data files identified at 610 can be assigned to a new file set (e.g. DetectedFileQueue). The new file set (DetectedFileQueue) may be used to maintain a list of medical image data files stored on the remote image storage memory component that have not yet been copied to the central storage memory, and have not been confirmed to be completed on the remote image storage memory. The DetectedFileQueue may be arranged as a list stored in the central storage memory.

The files in the new file set may be ordered based on various criteria. For example, the files may be ordered based on a First-In-First-Out (FIFO) order. This provides a simple arrangement for collecting medical image data files in order of detection by the central processor. Alternatively, other ordering criteria may be used such as Last-In-First-Out (LIFO) or First-In-Last-Out (FILO) techniques.

In some cases, the new file set may be ordered based on file properties associated with each of the medical image data files. Each medical image data file may be assigned a priority value indicating the importance of copying the corresponding medical image data item to the central storage memory. The priority value may be assigned by various components, such as the imager or central processor. The priority value may be determined based on an expected request time period (e.g. when the medical image data item is expected to be requested by a user of the image management system).

In some cases, the priority values assigned to medical image data files may vary over time. For instance, the priority value may increase over time to ensure that older medical image data files are copied before they are deleted from a source memory location. Priority values may also be updated based on inputs received from the central processor corresponding to the particular medical image data files. For instance, inputs indicating a follow-up appointment for the corresponding patient or a request for the medical image data file or related medical image data files may trigger an update to the priority values.

In some cases, other file properties may also be used, such as the particular remote image storage memory location or size of various medical image data files. In some cases, the medical image data files may initially be grouped based on their assigned priority value. Each group of files may then be arranged using FIFO, LIFO, or FILO criteria as previously discussed.

The central processor can determine that a new medical image data file has reached a "to be copied" position in the new file set. For instance, the "to be copied" position may be the top (i.e. first) position in the new file set (e.g. DetectedFileQueue), or a first plurality of positions in the new file set.

When a new medical image data file has reached a "to be copied" position in the new file set, the file characteristics of the medical image data file may be updated. The updated file characteristics can be compared to the file characteristics associated with the medical image data file from the time of allocation to the new file set. If the file characteristics have changed, the central processor may determine that storage of the new medical image at the remote image storage memory has not completed (or at least, may indicate that further review is required to ensure that storage has been completed).

In some cases, the new file set may also include a delay period between the allocation of a new medical image data file to the new file set and when that new medical image data file is permitted to reach the "to be copied" position. This may allow the central processor time to monitor/identify any changes to the file characteristics after a file is detected.

An expected complete set of file characteristics may also be determined for the medical image data file. The expected complete set of file characteristics may be determined based on the data format of the medical image data file. The file characteristics for the new medical image data file may be compared to the expected complete set of file characteristics to ensure that storage of the medical image data file has been completed. The new medical image data file may be determined to be a completed medical image data file when its file characteristics match the expected complete set of file characteristics.

The configuration of the new file set or DetectedFileQueue (and even method 600 in general) may vary in different implementations of a file collection process. For example, a single new file set may be used for medical image data files from all the remote image storage memory locations with which a central processor communicates. This may provide a streamlined order for the collection process, in particular for implementations with lower volume of medical images being generated.

Alternatively, separate new file sets may be used for each remote image storage memory location. For instance, a separate new file set may be used for each medical imager in a healthcare facility. This may simplify determining which medical image data files to copy in larger facilities with a high volume of medical image data files being generated.

In some cases, the particular configuration of the new file set may vary over time. For instance, the relationship between the new file sets and remote image storage memory locations may be dynamically configured based on the required performance and data volume size being generated.

In some cases, each new file set may be used for medical image data files of the same type. For example, there may be one or more new file sets for each imaging type and format of medical image data files generated. Various other configurations and combinations of new file sets may be used, as will be apparent to a person skilled in the art.

Once it is determined that storage of the medical image data file has been completed on the remote image storage memory, the central processor can determine that the medical image data file is ready to be copied to the central storage component. The central processor may then copy the new medical image data file to the central storage memory at 630.

In some cases, the new medical image data file may be assigned to a completed file set (e.g. CompletedFileQueue). Copying of new medical image data files may then occur based on the position of the medical image data files within the completed file set. The completed file set and ordering of the completed file set may be performed in various manners, as explained above in reference to the new file set. As with the new file set, the completed file set may also be configured for one or more remote imagers. In some cases, multiple completed file sets may be used by central processor to arrange the copying of medical image data files from remote image storage memory locations.

An example process for copying completed medical image data files is shown in Table 3:

TABLE 3

Example Process for Copying Completed Medical Image Data Files

| Step | Action |
|---|---|
| 1 | Read/Receive next available file from CompletedFileQueue |
| 2 | Copy the file from the remote image storage memory to the local/central storage memory |
| 3 | Move file identifier from the CompletedFileQueue to the CopiedFileQueue |
| 4 | Add file identifier to database on the central storage memory |
| 5 | Go to step 1 |

A medical image data file can be copied to the central storage memory associated with the central processor. The medical image data file can be stored in the central storage memory in its original format. The unique file identifier of the medical image data file may then be stored in an image source database on the central storage memory. The image source database may include unique file identifiers for each of the medical image data files copied from a particular remote storage memory location. In some cases, the image source database may be segregated into different database records for different remote storage memory locations. The some cases, the image source database may provide a combined record for all of the remote storage memory locations in communication with the central processor.

The image source database may also store related file information associated with each file identifier. The related file information may include the source location for the medical image data file. The source location may include the date/time the medical image data file was collected as well as the full source address/location path from which the medical image data file was collected. The related file information may also include the current storage location for the medical image data file. The current storage location may identify the address at which the medical image data file is stored on the central storage memory.

Once the medical image data file is copied, the file identifier may be moved from the completed file set to a copied file set (e.g. CopiedFileQueue) on the central storage memory. The copied file set may indicate that the medical image data file is present on the central storage memory to be accessed and/or for further processing. The copied file set may be implemented in various configurations as described above with reference to the new file set and completed file set.

At 640, the central processor can determine an expected set of files corresponding to the copied image data file. The expected set of files may define the medical image data item of which the copied image data file is a part. The expected set of files may include one or more medical image data files that, together, form the medical image data item generated on the remote storage memory.

The set of files that define a medical image data item generally refers to the group of files generated from one imaging process/procedure (e.g. a whole slide imaging scan, an endoscopy video, a CT scan etc.). The set of files that define a medical image data item may vary depending on the type of medical image. The set of files that define a medical image data item may also depend on the imager and/or imaging software used to capture the medical image and generate the medical image data item.

The central processor may determine the expected set of files based on characteristics of the copied image data file, such as file format, image type, imager type/brand, and imager software type etc. For instance, the central processor may determine a format of the copied image data file. The central processor may then determine the expected set of files based on the identified format of the copied image data file.

For example, an Aperio Digital Pathology Slide Scanner may generate a medical image data item as a single medical image data file with an .svs extension that is TIFF formatted and has proprietary data and file properties added. In this case, the set of files for the medical image data item may include the single medical image data file.

Other imagers may generate a medical image data item as a named folder that includes a file subdirectory. The file subdirectory may include an index file and a plurality of pixel files that each store the complete set of pixel data for a specific level/scale of WSI image. The medical image data files in the subdirectory (i.e. the index file and the pixel files) may then constitute the set of files for the medical image data item.

In some cases, the central processor may determine the expected set of files based on previously copied medical image data items. For instance, the central processor may monitor the set of files collected for previous medical image data items from the same remote image storage memory location. The central processor may then determine the expected set of files to correspond to the set of files copied for previous medical image data items from the same storage component (or generated by the same imager or type of imager).

In some cases, the central processor may determine the expected set of files prior to copying the image data file. Alternatively, the central processor may determine the expected set of files after the image data file has been copied to the central storage memory.

The central processor can define a unique set identifier for the set of files that define the medical image data item. The unique set identifier may identify unique file identifiers for each of the medical image data files in a particular medical image data item.

In some cases, the expected set of files for a copied image data file may have been previously determined based on a previously copied image data file for the same medical image data item. In such cases, the expected set of files may be determined using the unique file identifier for the copied image data file to identify the corresponding unique set identifier for the expected set of files.

At 650, the central processor can determine that all of the files in the set of files identified at 640 have been copied to the central storage memory. For instance, the central processor may compare the unique file identifiers defined in a unique set identifier to the file identifiers stored in the image source database. If all of the unique file identifiers match a file identifier in the image source database, the central processor can determine that all of the files have been copied.

The central processor can then generate an indicator at 660 that a medical image data item is available at the image management component. The indicator generated at 660 may indicate that the medical image data item is available for further processing by the central processor (e.g. according to method 700 shown in FIG. 7 and described herein below).

The indicator may also indicate that the medical image data item is accessible to be reviewed and/or transferred to external systems. In some cases, generating the indicator may also introduce the medical image data item (or corresponding representative objects) into workflows defined by the central processor or related image management components.

In some cases, the central processor may determine that the set of files for a particular medical image data item was never created at the remote image storage memory component. For instance, this may occur where there was an error during creation of the image data item and a re-scan may be initiated. In such cases, the central processor may delete the medical image data files that were copied as the complete medical image data item will not become available.

After a medical image data item is copied to the central storage memory, the central processor may ignore the subsequent deletion of that data item on the remote storage memory. Accordingly, the subsequent deletion of that data item on the remote image storage memory would not result in that data item being deleted from the central storage memory. This may ensure that the central storage memory controls the storage and management of medical image data items, independently of the data management policies implemented by imagers and/or remote image storage memory. For instance, some remote image storage memory locations may periodically delete data items to account for limited storage capacity.

As mentioned, the unique file identifiers can be generated by the central processor independently of the file characteristics of the medical image data files on the remote storage memory. Accordingly, when a new medical image data file is generated at the remote image storage memory with the same file name as a previously copied medical image data file, the central processor can assign a different unique file identifier to the new medical image data file. This new medical image data file can then be copied to the central storage component as a separate medical image data file.

In some cases, the remote storage memory may update/modify a medical image data file stored thereon. The central processor may identify the updated medical image data file as a new data file and assign a new unique identifier to the updated medical image data file. The central processor may then copy the updated medical image data file to the central storage memory as a separate medical image data file from the previously copied data file.

For example, an imager associated with a remote image storage memory location may determine that a rescan or reimage is required for the same subject (e.g. the same tissue slide or the same patient. The result of such a re-scan may be stored in the remote image storage memory with the same file name as the original scan or image data item. The central processor may identify the rescanned image data item as a separated data item with a different unique identifier.

In some cases, the remote image storage memory locations may store medical image data items and medical image data files in a format that is not compatible with a central image management system. For example, the medical image data items may not be stored in a DICOM-compatible format. Accordingly, a conventional PACS 106 may be unable to collect the medical image data items from the remote storage memory.

In such cases, the collected medical image data items may be stored in an external or additional image management component that communicates with PACS 106, such as LIM 104. The image collection system may provide the collected medical image data items for further processing by components of an image management system such as LIM 104. In some cases, the collected medical image data items may also be arranged in a processing set or processing file set to define the order in which the collected medical image data items are processed. The processing set (or CopiedItemQueue) may be structured and operate similar to the above-mentioned sets, such as the new file set, the completed file set and the copied file set.

Representative objects that are DICOM-compatible may be generated from the collected medical image data items and provided to PACS 106 to be incorporated into the PACS 106 workflows. For example, the collected medical image data items may be processed using embodiments of method 700 for processing medical image data items.

Processing Large Image Data Items

The following is a general description of systems and methods for processing medical image data items and other features set out herein that may be used by itself or in combination with one or more embodiments disclosed herein, including systems and methods for managing medical image data items, systems and methods for collecting medical image data items, and systems and methods for transferring medical image data items. The following description contains various features of systems and methods for processing medical image data items which may be used individually or in any combination or sub-combination.

The systems and methods for processing medical image data items described herein may be implemented as part of an image management system, such as image management system 100. For instance, embodiments of method 700 for processing medical image data items may be implemented by LIM 104 and PACS 106 of image manager 102.

Medical image data items can be generated with varying data sizes and in a variety of formats. In some cases (as with many large medical image data items), the medical image data items may be generated in imager-specific or proprietary format. As a result, medical image data items may be separated into different image management systems based on department or image type. These medical image data items may not easily integrate into centralized or combined image management systems.

Many centralized healthcare systems (e.g. PACS, HIS, RIS etc.) may use defined communication formats/protocols that are DICOM-based. However, as many of the medical image data items are not generated to be compatible with these DICOM-based systems, they remain siloed and may not be accessible through the centralized healthcare management interface.

Even when DICOM-compatible images are generated, it may be inefficient to incorporate the entire large medical image data item directly into the image management workflows. The DICOM protocols are primarily concerned with standardized communication and data exchange between DICOM devices (often referred to as application entities). The performance and efficiency of communication and data transfer are not emphasized in the workflows generated by DICOM-based systems such as conventional PACS 106.

While standard DICOM communication protocols may allow medical image data items to be transferred between devices, it may not be reliable or sustainable to frequently use this approach with large medical image data items with data sizes in the Gigabyte and Terabyte range. Accordingly, embodiments described herein may process medical image data items (both proprietary and DICOM-formatted data items) to generate derived objects that may facilitate storage, processing, and retrieval within an image management system such as image manager 102 and/or PACS 206. Some or all of these derived objects can be generated with a data size that is confined to a limited or restricted maximum data size that is smaller than the data size of the medical image data items (in some cases, thousands of times smaller). For example, representative objects can be generated according to a restricted maximum data size defined as 100 MB in some cases. In other examples, representative objects can be generated according to a restricted maximum data size defined as 10 MB.

The embodiments described herein may also include systems and methods for processing medical image data items. Each medical image data item can include at least one medical image set from the same imaging procedure (e.g. from the same tissue sample, X-Ray scan, endoscopy video etc.). Each medical image set defines a sub-image from the imaging procedure. In some cases, a medical image set may define the sub-image as a whole (i.e. a single sub-image region). In other cases, the medical image set may separate the sub-image into a plurality of sub-image regions or sections.

A medical image data items can be processed to identify image metadata and image pixel data. In some cases, the image pixel data may be extracted from the medical image data item.

The pixel data can be used to generate a plurality of pixel objects that, together, include all of the pixel data from the medical image data item. Each individual pixel object may include the pixel data for a sub-image (e.g. a z-plane, or slice), for a region within a sub-image (e.g. a tile or a sub-section of a slice), or for multiple regions in the sub-image. The pixel objects may be stored and retrieved independently, to provide added storage flexibility. The pixel objects may also be individually addressable in memory, providing the ability to access, modify or retrieve only the sub-images or sub-image regions needed.

The image metadata may be used to generate representative objects. The representative objects may include one or more set representative objects. The representative objects can include a set representative object corresponding to each medical image set and defining identifying characteristics for the sub-image defined by that medical image set.

The set representative objects may be generated as representative metadata objects. Each representative metadata object may define identifying characteristics of a sub-image of the medical image defined by the medical image data item. In some cases, the representative metadata objects may be generated in a format corresponding to a communication protocol used by core components image management system, such as the DICOM protocol used by core components of a PACS.

In some cases, the representative objects may also include a global representative metadata object that defines identifying characteristics of the medical image as a whole or group.

The derived objects may also include one or more pixel metadata objects. The pixel metadata objects can include identifying metadata defining identifying characteristics of individual pixels objects. The pixel metadata objects can also include relational metadata defining relationships between the individual pixel objects. For instance, the relational metadata may define the spatial relationships between the individual pixel objects. The relational metadata may indicate how a sub-image or the whole medical image may be reconstructed from the pixel objects.

The representative objects may also include one or more overview objects. Each overview object may include both overview object metadata and overview pixel data. The overview pixel data may provide a representation of the medical image or a sub-image at a lower resolution than that defined by the corresponding pixel object. The overview object metadata may include a portion of the image metadata corresponding to the medical image or sub-image being representative. In some cases, the overview objects may be generated in a format corresponding to a communication protocol used by core components image management system, such as the DICOM protocol used by core components of a PACS.

In some cases, the systems and methods for processing medical image data items may be used with systems and methods for managing medical image data items and/or systems and methods for collecting medical image data items described herein.

Referring now to FIG. 7, shown therein is a flowchart of a method 700 for processing medical image data items in accordance with an example embodiment. In some cases, method 700 may be implemented as an image processing application within an image management system. For example, method 700 may be implemented using image manager 102. Method 700 may also be implemented by an imager or medical imaging system.

At 710, a medical image data item can be received or identified. The medical image data item may be received from various external and/or internal image storage memory locations. In some cases, the medical image data item may be identified in the storage memory of a system implementing method 700.

The medical image data item may be collected as part of an image collection process, such as example process 600 described above with reference to FIG. 6. Alternatively, the medical image data item may be stored in an image archive, such as image archive 230 shown in FIG. 2 described above. The medical image data item may also be stored in storage memory associated with a medical imager.

In some cases, the medical image data item may already be stored within an image management system, such as by PACS 106/206 or by LIM 104/304. Alternatively, the medical image data item may be received from an external image management system, such as a PACS or image manager associated with a different healthcare institution.

The medical image data item may be received in various formats. In some cases, a medical image data item may be received in non-DICOM formats. For example, the medical image data item may be received in proprietary formats or proprietary formats based on open-source formats such as TIFF, JPEG, and BMP.

In some cases, the medical image data item may be received in a DICOM-compatible format. For example, the medical image data item may be generated in a DICOM WSI format.

The medical image data item generally includes one or more medical image sets from the same medical imaging procedure. In general, a medical image set defines a sub-image of the medical image data item. Accordingly, each medical image set can include at least one sub-image object that corresponds to the sub-image defined by that medical image set.

In some cases, each medical image set may correspond to a single sub-image object that defines the medical image set. Alternatively, multiple sub-image objects may correspond to a medical image set, for instance with each sub-image object defining a region of the corresponding sub-image.

For example, a sub-image may refer to a frame of endoscopy video medical image data item. A sub-image may also refer to a focal plane in a medical image stack generated from a single tissue sample. A sub-image may also refer to a slice of a volumetric imaging series. In some cases, the medical image data item may include sub-images with different resolutions. Accordingly, each medical image set can have a corresponding resolution.

In some cases, a medical image data item may only include a single sub-image. Accordingly, a medical image data item may have only one medical image set in some cases. For example, a tissue sample slide digitized with a single focal plane may correspond to a medical image data item with a single sub-image (i.e. the focal plane).

The received medical image data item generally includes one or more medical image data files. The one or more medical image data files, together, form the medical image data item. The one or more medical image data files are generated by the same medical imaging procedure.

A data item identifier or unique item identifier can be generated for the received medical image data item. For instance, the data item identifier may be generated as a unique set identifier.

At 720, image metadata and image pixel data can be identified in the medical image data item. For example, the image metadata and image pixel data may be identified based on the file format of the received medical image data item (e.g. as explained above with reference to parser 346).

The format of the medical image data item received at 710 may be identified. The number and type of medical image data files defining the medical image data item may be identified based on the determined format. Similarly, the medical image data files and the portions of medical image data files storing the image metadata and image pixel data respectively may be determined based on the identified file format.

For example, a medical image data item may be generated by an Aperio imager. Accordingly, the format of the medical image data item may be identified as a modified TIFF format corresponding to the Aperio imager. The medical image data item can then be parsed to extract the TIFF formatted/encoded attributes. The extracted TIFF attributes can be further parsed to identify the Aperio-specific attributes based a definition of the Aperio format. The extracted TIFF attributes and Aperio-specific attributes are used to define the image metadata and image pixel data.

Once the image metadata and image pixel data are identified, the image metadata and image pixel data may be extracted from the analyzed medical image data items. Derived objects such as pixel objects, representative objects and/or pixel metadata objects may then be generated from the extracted image metadata and/or image pixel data. These derived objects may be used to facilitate storage, management and processing of the medical images defined by the medical image data items.

In some cases, the location of the image metadata and image pixel data within the medical image data item may be stored for subsequent processing. For example, a mapping may be stored for the medical image data item that identifies the location of the image metadata and image pixel data within the medical image data item.

In some cases, some or all of the derived objects may not be stored permanently. For example, a medical image data item can be stored permanently in its original format and the derived objects may be generated on demand (e.g. in response to requests for images). Accordingly, storing a mapping of the image metadata and image pixel data within, or associated with, the medical image data item may facilitate subsequent generation of derived objects.

In some cases, the medical image data item may be processed to generate additional image metadata. The additional image metadata may then be included with or in addition to the image metadata extracted from the medical image data item.

In some cases, the pixel data corresponding to one or more sub-images of the medical image data item may be analyzed to identify sub-image metadata that can be included as part of the additional image metadata. The pixel data may be analyzed to identify sub-image properties. The sub-image properties may be used to provide an indication or estimate of the importance of a particular sub-image. For example, the estimate of sub-image importance may reflect an estimate of how likely it is that the sub-image includes pixel data of diagnostic value or importance.

The pixel data may be analyzed to identify potential tissue pixel data within a sub-image. For example, a process for identifying a breast boundary and breast window within a medical image data item are described in U.S. Pat. No. 8,649,578 the entirety of which is incorporated herein by reference. Sub-image metadata indicating the presence of a breast window and/or the location of a breast window within the sub-image may then be included with the extracted image metadata.

In some cases, the sub-image properties may include stain properties that indicate the possible presence of stains in a sub-image or sub-image region. In some cases, the sub-image properties may include artifact properties indicating whether the sub-image includes image artifacts.

In some cases, the sub-image properties may include focus or sharpness properties indicating whether the sub-image is in or out of focus, and the level of sharpness of the sub-image. This may provide an indication as to whether a clinician is likely to observe pixel data of diagnostic quality within the sub-image.

In some cases, the additional sub-image metadata may include user-specific metadata corresponding to a user requesting the medical image data item or who is likely to request the medical image data item. For example, the pixel data from the sub-images may be compared with pixel data from sub-images previously accessed and used diagnostically by a clinician. The sub-image properties for sub-images that are similar to those previously used for diagnosis may indicate an increased importance estimate.

At 730, a plurality of pixel objects can be generated from the image pixel data. Each pixel object corresponds to one of the sub-images in the medical image data item. Each sub-image can have at least one corresponding pixel object in the plurality of pixel objects.

Each pixel object generally includes at least a portion of the image pixel data identified in the medical image data item. Each portion of the image pixel data can be stored in one of the pixel objects generated at 730. Accordingly, the plurality of pixel objects can provide a complete collection of the pixel data from the medical image data item received at 710.

Each pixel object also includes a pixel object identifier with identifying characteristics of that pixel object. The pixel object identifier can identify the data item identifier corresponding to that pixel object. The pixel object identifier can also identify the sub-image corresponding to that pixel object.

Each sub-image may have one corresponding pixel object. For example, where the medical image data item is a volumetric series, each slice may be stored as a single pixel object. Similarly, pixel objects may be generated for each slice for CT/MR/US images, each frame for endoscopy videos, each slice a Cardio scans etc.

In some cases, a plurality of pixel objects may be generated for a sub-image. For example, the pixel data corresponding to a sub-image may be separated into a plurality of sub-image regions. A pixel object may then be generated for each sub-image region that includes the corresponding pixel data for that region. For example, a pixel object may be generated for each tile of a digitized pathology slide.

In some cases, the medical image data item may include pixel data for one or more sub-images at multiple resolutions. One or more pixel objects may then be generated for each resolution of a particular sub-image.

At 740, the pixels objects can be stored in a first memory location. In different embodiments, the first memory location may correspond to storage memory associated with various sub-systems of image management and healthcare file management systems. Each pixel object can be stored at a corresponding pixel object address location in the first memory location. Each pixel object may be individually addressable at its corresponding pixel object address location.

For example, in some cases the pixel objects may be stored in a LIM 104. Storing the pixel objects in LIM 104 may remove the pixel objects from the storage workflows of core PACS 106 components.

In some cases, pixel objects may be stored in a storage memory associated with an imager 110. In some cases, the pixel objects may be stored in an image archive such as image archive 230. In some cases, the first memory location may even be a storage memory associated with a PACS 206.

In some cases, the pixel objects may be stored as a block or group of pixel objects. The block of pixel objects may include all of the pixel objects in the plurality of pixels objects stored adjacent one another in the storage memory. This may facilitate storage and retrieval of consecutive pixel objects, e.g. by storing pixel objects adjacent to related pixel objects.

In some cases, the pixel objects can be stored independently. That is, the address location in the first memory at each pixel object is stored can be determined independently from the address location for every other pixel object. This may provide flexibility when storing pixel objects to account for storage capacity considerations, for instance without having to re-arrange how data is currently stored.

In some cases, groups of pixel objects may be stored collectively but independent from other groups of pixel objects. For instance, a group that includes the plurality of pixel objects corresponding to one sub-image may be stored as a block in the first memory, but independently of the groups including pixel objects corresponding to the other sub-images.

In some cases, each pixel object may be individually addressable in the first storage memory. Individually addressable pixel objects may facilitate the retrieval of pixel data in response to requests for sub-images or regions of sub-images. The pixel data corresponding to a requested sub-image or sub-image region may be directly recalled/retrieved based on the address location of the corresponding pixel object.

At 750, a plurality of representative objects can be generated for the medical image data item. The representative objects can be generated from the image metadata and/or image pixel data identified at 720. In general, the representative objects correspond to the medical image and sub-images of the medical image data item, but include less pixel data (e.g. lower resolution images or sub-images) or no pixel data. The representative objects can include representative metadata and/or representative pixel data reflective of the pixel data in the medical image data item but with a smaller (often substantially smaller) data size.

Each representative object also includes a representative object identifier that defines identifying characteristics of that representative object. The representative object identifier can identify the data item identifier corresponding to that representative object. The representative object identifier may also identify any sub-images or sub-image regions corresponding to that representative object. Accordingly, the representative objects and pixel objects for the same medical image data item (and corresponding sub-images) may be determinable from the data item identifier and the representative object identifier/pixel object identifiers.

The representative objects may be used with data management and lifecycle workflows related to the medical image data items while the pixel objects remain stored in the first memory location. The representative objects may also be used to provide user interfaces to users interested in medical image data items. For instance, the representative objects may identify the available pixel data and pixel objects stored in the first memory location. The pixel objects may then be retrieved as requested to provide higher resolution medical images and sub-images. This may facilitate the data management and workflows, without requiring large data objects to be incorporated into the workflows.

The representative objects may be stored in a second memory location. In some cases, the second memory location may be separate from the first memory location. For example, the first memory location may correspond to a LIM 104 or image archive 230 while the second memory location corresponds to a PACS 106/206.

The representative objects can be generated in a format that is compatible with workflows of an image management system. For example, the representative objects may be generated to be compatible with a defined communication protocol, such as the DICOM protocol used by a PACS 106/206. This may facilitate integration of the representative objects into the image management system and workflows. In some cases, the pixel objects may not be generated (or converted) into a DICOM format prior to storage.

The representative objects can be generated with a data size smaller than the medical image data items themselves to facilitate management within existing workflows. For instance, representative objects may be generated with a maximum data size of 100 MB in some examples. In some examples, representative objects may be generated with a maximum data size of 10 MB.

The representative objects can include representative metadata objects generated from the image metadata. Each representative metadata object may correspond to one of the sub-images of the medical image data item. Each representative metadata object can define identifying characteristics for the corresponding sub-image. In general, the identifying characteristics for a sub-image generally characteristics of that individual sub-image.

The identifying characteristics for a sub-image may include a data item identifier for the corresponding medical image data item, type of image, image resolution, available sub-regions (e.g. tiles), and memory location identifying the first memory location. The identifying characteristics for a sub-image can also include patient data, imaging study data, series data, imaging method data and the like.

In some cases, the memory location stored in the identifying characteristics may include a sub-image specific address indicating the memory address location of the corresponding pixel object or pixel objects in the first memory location. In some cases, the memory location stored in the identifying characteristics may include sub-image region specific address data for pixel objects corresponding to specific regions of a sub-image. For example, the representative metadata object may include a URL identifying the memory address location of the corresponding pixel object or pixel objects in the first memory location.

The representative metadata objects may be used with the standard procedures of an image management system. For example, the plurality of representative metadata objects may include all the metadata necessary to enable standard operations of the image management system such as workflows, images lifecycle management, viewing, reporting etc.

In some cases, the representative metadata objects may be generated in a DICOM-compatible format. For example, the representative metadata objects may be generated as DICOM headers. This may allow the representative metadata objects to be stored in a second memory location that is part of an image management system using the DICOM standard.

For example, the representative metadata objects may be stored in a PACS 106/206. The representative metadata objects may be used in the workflows defined by workflow activation component 114. The plurality of representative metadata objects may contain all the DICOM metadata required for PACS 106/206 functions such as workflows, image lifecycle management, viewing, reporting etc. In some cases, the representative metadata objects can be generated with a maximum data size of 1 MB. In other words, each representative metadata object can be generated so that its data size is 1 MB or less.

In some cases, the representative objects generated at 750 may also include at least one overview object for the medical image data item. Each overview object can include an overview pixel object and overview object metadata.

The overview pixel object can provide an overview of one or more sub-images of the medical image data item. For example, each overview pixel object may include a reduced resolution sub-image corresponding to one of the sub-images of the medical image data item. The reduced resolution sub-image may have an overview resolution that is less than the resolution of the pixel object corresponding to that sub-image.

In some cases, each overview pixel object may have a data size that is one thousand times less than a corresponding pixel object. In some cases, each overview pixel object may have a data size that is ten thousand times less than a corresponding pixel object.

For example, a medical image data item may define a medical image with pixel data that includes 256,000×256,000 pixels. A corresponding overview pixel object may be generated that is as small as 256×256 pixels. Accordingly, the reduced resolution sub-image is about 1,000,000 times smaller than the corresponding pixel data of the medical image data item.

In some cases, the at least one overview object may include a plurality of overview objects with an overview object corresponding to each sub-image of the medical image data item.

In some cases, the overview objects may include multiple overview objects corresponding to a particular sub-image each with a different overview resolution. That is, each of the plurality of overview objects corresponding to the same sub-image may have an overview pixel object with a different overview resolution. Each overview pixel object may provide a reduce resolution image or sub-image.

The overview object metadata can include a portion of the image metadata corresponding to the portion of the pixel data used to generate the overview pixel object (i.e. corresponding to the sub-image represented by the overview pixel object).

In some cases, the overview objects may be used as part of an image management system. For example, the overview objects may provide reduced resolution sub-images that can be displayed to a user interacting with the image management system, e.g. using a viewer 108. The overview objects may allow the user (physicians, clinicians, surgeons, etc.) to rapidly perform non-diagnostic reviews of the corresponding sub-image, using the reduced resolution overview pixel objects. In some cases, an overview object may even be sufficient for some aspects of a diagnostic review.

In some cases, the overview objects can be generated with a maximum data size of 10 MB. In other words, each overview object can be generated so that its data size is 10 MB or less.

The overview object metadata can also include a list of representative metadata objects corresponding to the same medical image data item. The overview object metadata may list each of the representative metadata objects corresponding to the same medical image data item. The overview object metadata may provide a link or URL to the listed representative metadata objects. The overview object metadata may also identify all the other overview objects available for the same medical image data item.

Similarly, the representative metadata objects can each include a list of all the overview objects for the same medical image data item. The representative metadata objects can also identify all the other representative metadata objects available for the same medical image data item. Thus, a user interacting with an image management system may select one of the representative metadata objects and/or overview objects and be provided with identifying information for all the related overview objects and/or representative metadata objects.

In some cases, accessibility criteria may be defined for the overview objects. For example, the accessibility criteria may restrict or limit access to certain overview objects based on user roles defined within an image management system. The accessibility criteria may control access to particular overview objects based on a user's role. For example, the accessibility criteria may provide some users with access only to overview objects with lower resolution overview pixel objects, while other users may have access to higher resolution overview objects (or all overview objects).

The overview object metadata for an overview object may be used along with the accessibility criteria and a user's defined role to determine if the user has access to the overview object. In some cases, the existence of a particular overview object may not be visible to a user unless their role qualifies to access that overview object based on the overview object metadata for the particular overview object and the overview accessibility criteria. In some cases, the accessibility criteria may provide a user with access to only one resolution of the overview objects for the medical image data based on the user's role.

The accessibility criteria may define a maximum accessible data size of the objects accessible to a particular user. A user requesting overview objects or pixel objects may then be limited to viewing overview objects or pixel objects whose data size is less than the maximum accessible data size. For example, the maximum accessible data size may be defined as 10 MB for a physician/clinician user while the maximum accessible data size is unlimited for a reading Pathologist.

In some cases, the overview objects may be generated in a DICOM-compatible format. This may facilitate integration of the overview objects into an image management system that operates using the DICOM protocol, such as PACS 106/206. For example, an overview object may be generated as a DICOM secondary capture object.

In some cases, the representative metadata objects may be omitted. For example, the overview objects may be generated to include overview object metadata that also includes all the metadata necessary for integration into image management systems and workflows. The overview object metadata may then be defined to include identifying characteristics for corresponding sub-images of the medical image data item.

Alternatively, the overview objects may be omitted. In such cases, the representative metadata objects may be used for both the image management workflows, as well as to provide information for a user interface. However, in such cases, a user may not be able to perform an initial review of a sub-image without requesting the corresponding pixel data stored in the first memory location.

At 760, at least some of the representative objects can be stored in a second memory location. The representative metadata objects and/or overview objects can be stored in the second memory location separate from the first memory location in which the pixel objects are stored.

The second memory location in which the representative objects are stored may be storage memory associated with an image management component that operates with a defined communication protocol. For example, the representative objects may be stored in a PACS 106 that uses the DICOM protocol.

In some cases, the second memory location may correspond to a fast-access storage component (e.g. a cache) while the first memory location is a slower storage component (e.g. an archive or long-term storage component) that may be located remote from a processed of the image management system. For example, the second memory location may be stored locally at an image management system while the first memory location is external to or remote from the image management system. This may allow the representative objects to be easily and rapidly retrieved for ongoing image management processes and workflows with the pixel objects retrievable as required.

In some cases, pixel metadata objects may also be generated for the medical image data item. The pixel metadata objects may correspond to the medical image sets and the corresponding pixel objects.

At least one set of pixel metadata objects may be generated, with each set corresponding to one of the medical image sets. Each set of pixel metadata objects can include identifying metadata defining the identifying characteristics for the pixel objects corresponding to that medical image set. Each set of pixel metadata objects may also include relational metadata defining spatial relationships between the pixel objects corresponding to that medical image set. The relational metadata can also include overall relational metadata identifying the spatial relationships between the pixel objects of different (e.g. adjacent) medical image set/sub-images.

For example, a medical image data item may be generated as a DICOM WSI data item. A DICOM WSI data item can include binary data that represents up to 11 million sub-images or sub-image regions (e.g. tiles.). The binary data may be included in a textual array adjacent the pixel data. The binary data may be extracted and used to define the pixel metadata objects. The pixel metadata objects may be generated as DICOM fragments (partial DICOM header objects).

The pixel metadata objects can be stored in the first memory location (or another memory location). As the pixel metadata objects include image metadata that defines spatial relationships between pixel objects stored in the first memory location they may not be required for the functions of an image management system unless the corresponding pixel objects are requested. As such, the pixel metadata objects may be stored external to the core components of an image management system.

In some embodiments the pixel objects, representative objects, and/or pixel metadata objects may be used with an image management system such as system 100 shown in FIG. 1. In such embodiments, the first memory location may correspond to LIM 104 and the second memory location may correspond to PACS 106.

The DICOM conversion process 700 may then be performed primarily by LIM 104 or by an external image processing system. The pixel objects generated at 730 can be stored in LIM 104. The LIM 104 may transmit the representative metadata objects and/or overview objects to PACS 106 as part of metadata message 116 or in a subsequent message or series of messages. The PACS 106 may then incorporate the representative metadata objects and/or overview objects into workflows defined by workflow activation component 114.

In some examples, the set of representative objects generated by a LIM 104 can include both representative metadata objects and overview objects. The set of representative objects can be provided to a core image management system, such as PACS 106. The overview objects may be generated as conventional DICOM objects that include both overview pixel data and overview object metadata. The representative metadata objects may only include image metadata as well as perhaps a URL to corresponding pixel data in the LIM 104.

A user of viewer 108 may interact with PACS 106 to review and request data related to medical image data items. The viewer 108 may include the representative metadata objects and/or overview objects in a graphical user interface presented to the user based on objects received from the PACS 106 in viewer messages 118. The user may initiate a request 120 for a medical image, e.g. by selecting one of the representative objects displayed in the user interface. In some cases, the user may review one or more of the overview objects prior to, or in place of, requesting pixel data for the medical image.

If the request 120 corresponds to a medical image data item having pixel data stored in LIM 104 (e.g. a large medical image data item), the request 120 can be re-routed to LIM 104. The LIM 104 can then transmit an image response message 124 to the viewer 108 with a pixel object that includes requested pixel data.

In some cases, the viewer 108 may be equipped to display multiple pixel objects. In such cases, the LIM 104 may also include the required pixel metadata objects in the response 124.

In other cases, a user of the viewer 108 may request a related pixel object (e.g. an adjacent pixel object) subsequent to receiving the pixel object in response 124. The LIM 104 may then use the stored pixel metadata objects (i.e. the relational metadata) to identify the correct pixel object to provide to viewer 108.

Embodiments described herein may provide image processing systems and methods that convert a medical image data item into a plurality of derived objects. The derived objects can include pixel objects and representative objects. In some cases, the derived objects may also include pixel metadata objects. The representative objects may be integrated into general image management and lifecycle workflows while the pixel objects are stored external from the core image management system. This may provide the high efficiency and throughput for managing the objects, while still allowing access to the high resolution pixel objects upon request.

In general, the derived objects such as the pixel objects, representative metadata objects, representative overview objects, pixel metadata objects and the original medical image data item may each include an item identifying corresponding to the medical image data item. This allows each of the objects and files relating to the same medical imaging procedure to be easily identified within an imaging system.

In some cases, the original medical image data item may be stored in its original state to prevent modifications. For example, a digital signature may be defined for each original medical image data item. The digital signature may indicate that the original medical image data item has not been modified from its original state. The digital signature may be configured to be modified or deleted if any modifications are made to the original medical image data item. In such cases, the derived objects may be generated by reading and/or extracting image metadata and image pixel data without modifying the original image metadata or image pixel data.

Transferring Large Image Data Items

The following is a general description of systems and methods for transferring medical image data items and other features set out herein that may be used by itself or in combination with one or more embodiments disclosed herein, including systems and methods for managing medical image data items, systems and methods for collecting medical image data items, and systems and methods for processing medical image data items. The following description contains various features of systems and methods for transferring medical image data items which may be used individually or in any combination or sub-combination.

Figure 8:
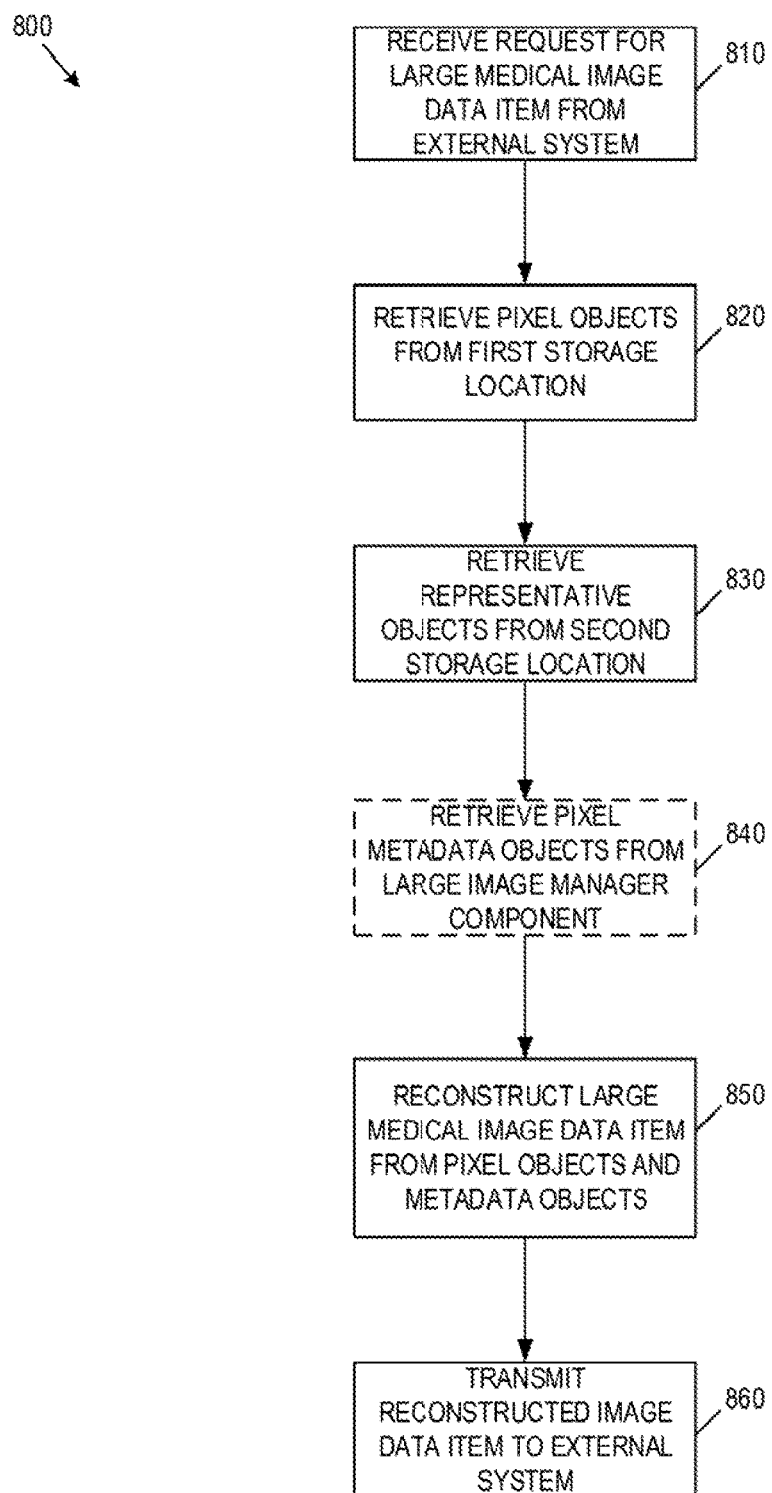
FIG. 8 is a flowchart illustrating a method of transmitting a medical image data item to an external system in accordance with an example embodiment.

Referring now to FIG. 8, shown therein is a flowchart of a method 800 for managing medical images in accordance with an example embodiment. In general, method 800 may be used to transfer medical image between remotely located image storage locations.

For example, method 800 may be implemented using an image management system such as system 100 shown in FIG. 1, PACS 204 shown in FIG. 2, and/or LIM 304 shown in FIG. 3. In some cases, method 800 may be implemented as an image transfer application on an image management system such as image manager 102.

Alternatively, method 800 may be implemented between two PACS 206 systems or between any two image storage components.

At 810, a request for a large medical image data item can be received from an external system. For example, the request may be received by PACS 106/206 or LIM 104/304. The request may identify a defined communication format/protocol (e.g. DICOM) for the requested medical image data item.

At 820, pixel objects for the large medical image data item can be retrieved from a first storage location. For example, the pixel objects may be stored in a LIM 104 or image archive 230 external to the core components of the image management system that received the request. In general, the pixel objects define pixel data for sub-images or sub-image regions within the medical image data item. The set of pixel objects for the large medical image data item generally includes all the pixel data for that medical image data item.

At 830, representative objects for the large medical image data item can be retrieved from a second storage location. For example, the representative objects may be stored in a storage component that forms part of the core image management system that received the request, such as a PACS 106/206. In general, the representative objects include metadata associated with the medical image data item as a whole or with sub-images as a whole. For instance, the metadata included in the representative objects may reflect resolution levels, patient data, image type, imager type, available sub-images etc.

Optionally at 840, pixel metadata objects for the large medical image data item can be retrieved from the first storage location. The pixel metadata objects may be stored along with the pixel objects, e.g. in a LIM 104 or image archive 230 external to the core image management system that received the request. The pixel metadata objects may define characteristics of the individual pixel objects as well as spatial relationships between the individual pixel objects. In some cases, the pixel metadata objects may not be required, e.g. where the metadata is stored as part of the representative objects retrieved at 830.

At 850, the large medical image data item can be reconstructed using the pixel data and metadata from the pixel objects, the representative objects and optionally the pixel metadata objects. The large medical image data item may be reconstructed into a combined medical image data object that includes metadata from the representative objects (and optionally the pixel metadata objects) and pixel data from the pixel objects. The combined medical image data object may be defined in accordance with the requested transmission format, e.g. DICOM.

Figure 9:
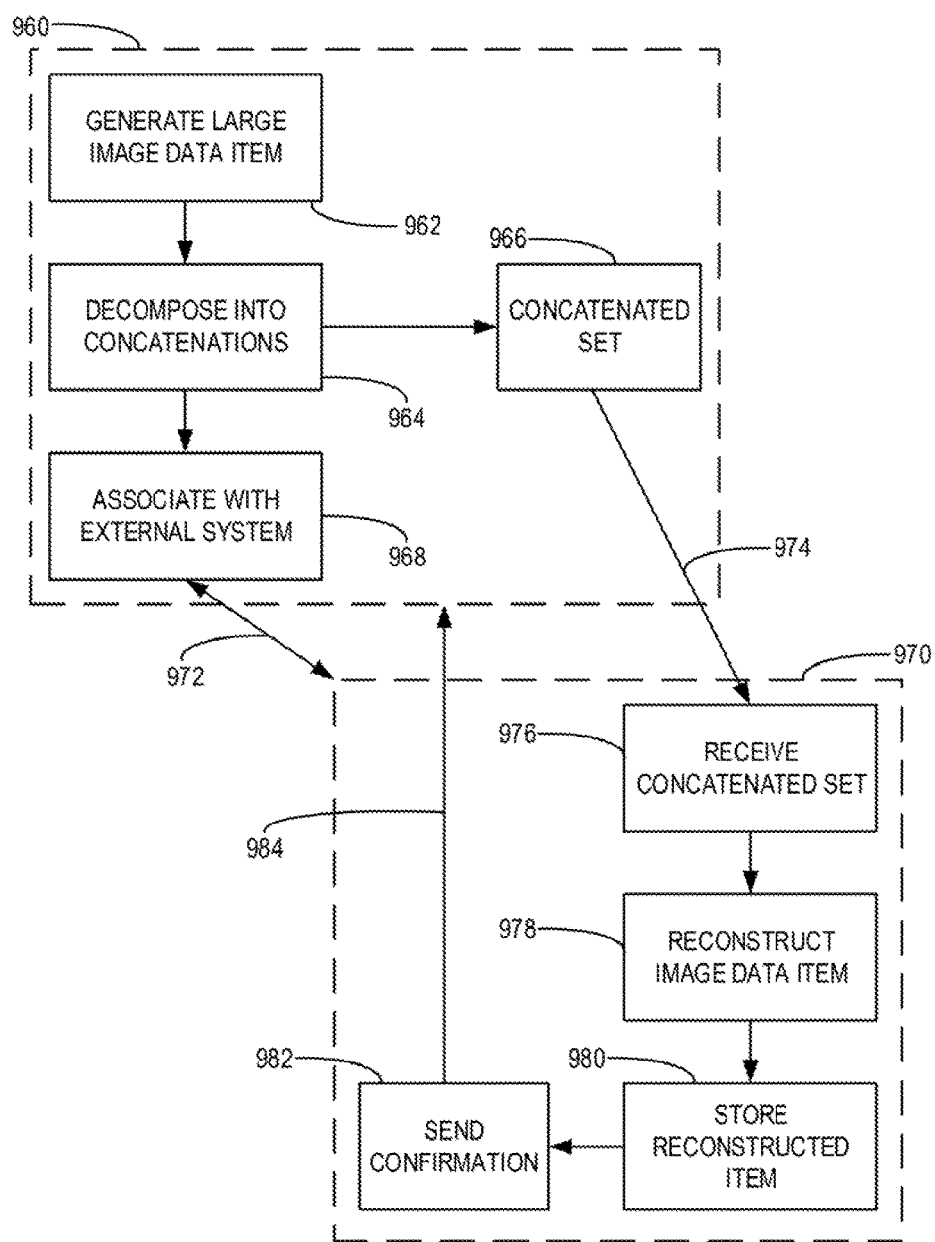
FIG. 9 is a block diagram illustrating the transmission of a large medical image data item between image management systems in accordance with an example embodiment.

At 860, the reconstructed combined medical image data object can be transmitted to the external system, an example of which is shown in FIG. 9.

Referring now to FIG. 9, shown therein is a block diagram 900 illustrating transmission of a medical image data item between a first image system 960 and an external system 970 in accordance with an example embodiment. For example, the medical image data item transmitted in block diagram 900 may correspond to the combined medical image data object generated at 850.

In some cases, the first image system 960 may be a PACS 106/206 associated with a first healthcare provider or facility while the second image system 970 is a PACS 106/206 associated with a second external healthcare provider or facility. Alternatively, the first image system 960 may be a LIM 104 while the second image system is a PACS 106/206. Various other systems may be used as first image system 960 and external system 970.

Block diagram 900 illustrates an example image transfer process that may be used to implement step 860 of method 800. Block diagram 900 is an example of how DICOM concatenations may be used to transmit large medical image data items between image management systems. Concatenations can be used to separate a single DICOM object into multiple DICOM objects or concatenations.

At 962, a large image data item is generated at first image management system 960. As mentioned, large image data item may be generated as described above in steps 810-880 of method 800. Alternatively, the large image data item may already be stored on the first system 960 (e.g. in storage memory of a LIM 104). In some cases, the large image data item may be generated according to the DICOM standard.

At 964, the large image data item is decomposed into a plurality of DICOM concatenations. The set of DICOM concatenations is then provided for transmission at 966.

At 968, an association is established between the first image system 960 and external system 970. Establishing the association may involve setting up a network communication channel between first image system 960 and external system 970. An exchange of association establishment messages 972 (i.e. a DICOM handshake) can be used to define low-level protocols for DICOM network connectivity to ensure that first image system 960 and second image system 970 are compatible and transfer data in a well-defined format and order.

Once the association is established, the concatenated set 966 is transmitted to external system 970 by transmission message(s) 974. The external system 970 completes receipt of the concatenated set at 976. The external system 970 can then reconstruct the large image data item from the concatenated set at 978, and store the reconstructed large image data item in local storage memory at 980. At 982, the external system 970 can transmit a confirmation message 984 to the first system 960 indicating the successful transfer of the large image data item.

The present invention has been described here by way of example only, while numerous specific details are set forth herein in order to provide a thorough understanding of the exemplary embodiments described herein. However, it will be understood by those of ordinary skill in the art that these embodiments may, in some cases, be practiced without these specific details. In other instances, well-known methods, procedures and components have not been described in detail so as not to obscure the description of the embodiments. Various modification and variations may be made to these exemplary embodiments without departing from the spirit and scope of the invention, which is limited only by the appended claims.

The invention claimed is:

1. A method of managing medical image data items, the method comprising:
  receiving a medical image data item, the medical image data item including at least one medical image set where each medical image set in the at least one medical image set is from the same medical imaging procedure and defines a sub-image from the medical imaging procedure, and each medical image set has a corresponding resolution and includes at least one sub-image object;
  defining a data item identifier for the received medical image data item;
  analyzing the received medical image data item to identify image metadata and image pixel data;
  generating a plurality of pixel objects for the medical image data item using the image pixel data, wherein each pixel object includes at least a portion of the image pixel data that corresponds to one of the sub-images, each sub-image has at least one corresponding pixel object, each portion of the image pixel data is included in one of the pixel objects, and each pixel object also includes a pixel object identifier that identifies the data item identifier and the sub-image corresponding to that pixel object;
  storing the plurality of pixel objects in a first storage memory with each pixel object having an address location in the first storage memory;
  generating at least one representative object for the medical image data item using the image metadata, the at least one representative object including a set representative object corresponding to each medical image set, and each set representative object defines identifying characteristics for the corresponding sub-image of the medical image set and identifies the first storage memory in which the corresponding at least one pixel object is stored, wherein the at least one representative object includes at least one overview object for the medical image data item, each overview object includes an overview pixel object and overview object metadata, the overview pixel object generated from a selected portion of the image pixel data and representing an overview of the medical image sets from the medical imaging procedure with an overview resolution that is less than the resolution of the image pixel data in the at least one medical image sets, and the overview object metadata includes a portion of the image metadata corresponding to the selected portion of the image pixel data and representative object identifiers identifying each of the at least one set representative objects; and
  storing the at least one representative object including the at least one overview object in a second storage memory.

2. The method of claim 1, wherein each pixel object corresponds to one of the sub-images and includes all the image pixel data from that sub-image.

3. The method of claim 1, wherein the address location for each pixel object is individually addressable in the first storage memory.

4. The method of claim 1, wherein, for each pixel object in the plurality of pixel objects, the address location in the first storage memory at which that pixel object is stored is determined independently from the address location for any of the other pixel objects.

5. The method of claim 1, wherein each set representative object comprises a representative metadata object that includes metadata defining the identifying characteristics for the corresponding sub-image and identifying the first storage memory in which the corresponding at least one pixel object is stored.

6. The method of claim 1, wherein generating the at least one overview object comprises:
  generating a plurality of overview objects for one of the medical image sets in the medical image data item, wherein each overview object in the plurality of overview objects has an overview pixel object with a different overview resolution.

7. The method of claim 6, further comprising:
  defining overview object accessibility criteria that controls access to each of the overview objects based on the overview object metadata and a role assigned to a user attempting to access the overview objects.

8. The method of claim 1, wherein:
  the second storage memory is accessible using a Picture Archive and Communication System (PACS) that communicates using a defined communication protocol; and
  each representative object is generated according to the defined communication protocol.

9. The method of claim 8, wherein the received medical image data item is in a fonnat that is not compatible with the defined communication protocol.

10. The method of claim 1, further comprising:
generating at least one set of pixel metadata objects, each set of pixel metadata objects corresponding to one of the medical image sets, and each set of pixel metadata objects including identifying metadata defining identifying characteristics for the pixel objects corresponding to that medical image set and relational metadata defining spatial relationships between the pixel objects corresponding to that medical image set.

11. The method of claim 10, further comprising storing the at least one set of pixel metadata objects in the first storage memory.

12. The method of claim 1, wherein the first storage memory and the second storage memory are remote from one another and are accessible via different image management systems.

13. A computer program product comprising a non-transitory computer-readable storage medium storing computer-executable instructions for configuring a processor to perform a method of managing medical image data items, wherein the method is defined according to claim 1.

14. A system for managing medical image data items comprising:
a first storage memory;
a second storage memory; and
at least one processor coupled to the first storage memory and the second storage memory, wherein the at least one processor is configured to:
receive a medical image data item, the medical image data item including at least one medical image set where each medical image set in the at least one medical image set is from the same medical imaging procedure and defines a sub-image from the medical imaging procedure, and each medical image set has a corresponding resolution and includes at least one sub-image object;
define a data item identifier for the received medical image data item;
analyze the received medical image data item to identify image metadata and image pixel data;
generate a plurality of pixel objects for the medical image data item using the image pixel data, wherein each pixel object includes at least a portion of the image pixel data that corresponds to one of the sub-images, each sub-image has at least one corresponding pixel object, each portion of the image pixel data is included in one of the pixel objects, and each pixel object also includes a pixel object identifier that identifies the data item identifier and the sub-image corresponding to that pixel object;
store the plurality of pixel objects in the first storage memory with each pixel object having an address location in the first storage memory;
generate at least one representative object for the medical image data item using the image metadata, the at least one representative object including a set representative object corresponding to each medical image set, and each set representative object defines identifying characteristics for the corresponding sub-image of the medical image set and identifies the first storage memory in which the corresponding at least one pixel object is stored, wherein the at least one representative object includes at least one overview object for the medical image data item, each overview object includes an overview pixel object and overview object metadata, the overview pixel object generated from a selected portion of the image pixel data and representing an overview of the medical image sets from the medical imaging procedure with an overview resolution that is less than the resolution of the image pixel data in the at least one medical image sets, and the overview object metadata includes a portion of the image metadata corresponding to the selected portion of the image pixel data and representative object identifiers identifying each of the at least one set representative objects; and
store the at least one representative object including the at least one overview object in the second storage memory.

15. The system of claim 14, wherein the at least one processor is configured to generate each pixel object to correspond to one of the sub-images and to include all the image pixel data from that sub-image.

16. The system of claim 14, wherein the at least one processor is configured to store each pixel object at an individually addressable address location in the first storage memory.

17. The system of claim 14, wherein, for each pixel object in the plurality of pixel objects, the at least one processor is configured to determine the address location in the first storage memory at which that pixel object is stored independently from the address location for any of the other pixel objects.

18. The system of claim 14, wherein the at least one processor is configured to generate each set representative object as a representative metadata object that includes metadata defining the identifying characteristics for the corresponding sub-image and identifying the first storage memory in which the corresponding at least one pixel object is stored.

19. The system of claim 14, wherein the at least one processor is configured to generate the at least one overview object by:
generating a plurality of overview objects for one of the medical image sets in the medical image data item, wherein each overview object in the plurality of overview objects has an overview pixel object with a different overview resolution.

20. The system of claim 19, wherein the at least one processor is configured to:
define overview object accessibility criteria that controls access to each of the overview objects based on the overview object metadata and a role assigned to a user attempting to access the overview objects.

21. The system of claim 14, wherein:
the second storage memory is accessible using a Picture Archive and Communication System (PACS) that communicates using a defined communication protocol; and
the at least one processor is configured to generate each representative object according to the defined communication protocol.

22. The system of claim 21, wherein the received medical image data item is in a format that is not compatible with the defined communication protocol.

23. The system of claim 14, wherein the at least one processor is configured to:
generate at least one set of pixel metadata objects, each set of pixel metadata objects corresponding to one of the medical image sets, and each set of pixel metadata objects including identifying metadata defining identifying characteristics for the pixel objects corresponding to that medical image set and relational metadata defining spatial relationships between the pixel objects corresponding to that medical image set.

24. The system of claim 23, wherein the at least one processor is configured to store the at least one set of pixel metadata objects in the first storage memory.

25. The system of claim 14, wherein the first storage memory and the second storage memory are remote from one another and are accessible via different image management systems.

* * * * *

UNITED STATES PATENT AND TRADEMARK OFFICE
CERTIFICATE OF CORRECTION

PATENT NO. : 10,559,378 B2
APPLICATION NO. : 15/436079
DATED : February 11, 2020
INVENTOR(S) : Kopylov Page 1 of 1

It is certified that error appears in the above-identified patent and that said Letters Patent is hereby corrected as shown below:

In the Claims

Column 62, Claim 9, Line 66: "fonnat" should read -- format --.

Signed and Sealed this
Fifteenth Day of September, 2020

Andrei Iancu
*Director of the United States Patent and Trademark Office*